United States Patent
Tomko et al.

(10) Patent No.: US 8,172,848 B2
(45) Date of Patent: May 8, 2012

(54) SURGICAL INSTRUMENTS FOR SPINAL DISC IMPLANTS AND RELATED METHODS

(75) Inventors: Daniel Tomko, Dallas, GA (US); Guilhem Denoziere, Powder Springs, GA (US); Stephan Eckhof, Weilheim (DE); Barbara Schweizer, Wurmlingen (DE); Alexander Geisser, Geisingen (DE)

(73) Assignee: SpineMedica, LLC, Marietta, GA (US)

( * ) Notice: Subject to any disclaimer, the term of this patent is extended or adjusted under 35 U.S.C. 154(b) by 1062 days.

(21) Appl. No.: 12/101,390

(22) Filed: Apr. 11, 2008

(65) Prior Publication Data

US 2008/0269756 A1   Oct. 30, 2008

Related U.S. Application Data

(60) Provisional application No. 60/914,471, filed on Apr. 27, 2007.

(51) Int. Cl.
  *A61B 17/56* (2006.01)
(52) U.S. Cl. .......................................... 606/87
(58) Field of Classification Search ............. 606/79, 606/87
  See application file for complete search history.

(56) References Cited

U.S. PATENT DOCUMENTS

| D245,919 S | 9/1977 | Shen |
| 4,759,766 A | 7/1988 | Buttner-Janz et al. .......... 623/17 |
| D312,309 S | 11/1990 | Michelson |
| 5,314,477 A | 5/1994 | Marnay .......................... 623/17 |
| 5,401,269 A | 3/1995 | Buttner-Janz et al. .......... 623/16 |
| 5,556,431 A | 9/1996 | Buttner-Janz et al. .......... 623/17 |
| 5,899,907 A | 5/1999 | Johnson |
| 6,425,920 B1 | 7/2002 | Hamada |
| 6,436,101 B1 | 8/2002 | Hamada |
| 6,793,658 B2 | 9/2004 | LeHuec et al. |
| 6,923,813 B2 | 8/2005 | Phillips et al. |
| 7,081,118 B2 | 7/2006 | Weber et al. ..................... 606/90 |
| 7,128,760 B2 | 10/2006 | Michelson |
| 2004/0143331 A1 | 7/2004 | Errico et al. |
| 2004/0143332 A1* | 7/2004 | Krueger et al. ............. 623/17.14 |
| 2004/0215198 A1 | 10/2004 | Marnay et al. |
| 2005/0043740 A1* | 2/2005 | Haid et al. ..................... 606/90 |
| 2005/0055099 A1 | 3/2005 | Ku .............................. 623/17.16 |
| 2005/0090829 A1 | 4/2005 | Martz et al. |
| 2005/0288788 A1 | 12/2005 | Dougherty-Shah |
| 2006/0064100 A1 | 3/2006 | Bertagnoli et al. |
| 2006/0116768 A1 | 6/2006 | Krueger et al. |
| 2006/0129160 A1* | 6/2006 | Liu et al. .......................... 606/85 |
| 2007/0179621 A1 | 8/2007 | McClellan, III et al. .. 623/17.16 |
| 2007/0276501 A1 | 11/2007 | Betz et al. ................... 623/17.16 |

FOREIGN PATENT DOCUMENTS

WO   WO 2006/033067   3/2006

* cited by examiner

*Primary Examiner* — Bruce E Snow
*Assistant Examiner* — Melissa Hoban
(74) *Attorney, Agent, or Firm* — Myers Bigel Sibley & Sajovec, P.A.

(57) ABSTRACT

Trials for spinal surgery include: (a) a trial implant portion having a shape corresponding to an implantable spinal disc implant; (b) a shaft connected to the trial implant portion; and (c) at least one axially extending cutting guide slot attached to the shaft at a position that is axially spaced apart from the trial implant portion, the cutting guide slot configured to releasably slidably receive and guide a cutting blade toward vertebral bone. Also described are additional surgical instruments, including, for example, pilot-hole punches, inserters, and methods of cutting keelways.

10 Claims, 29 Drawing Sheets

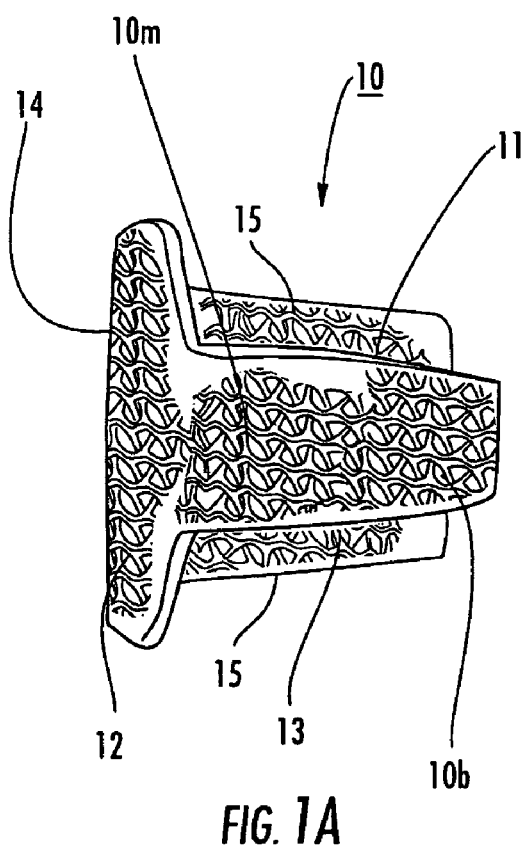
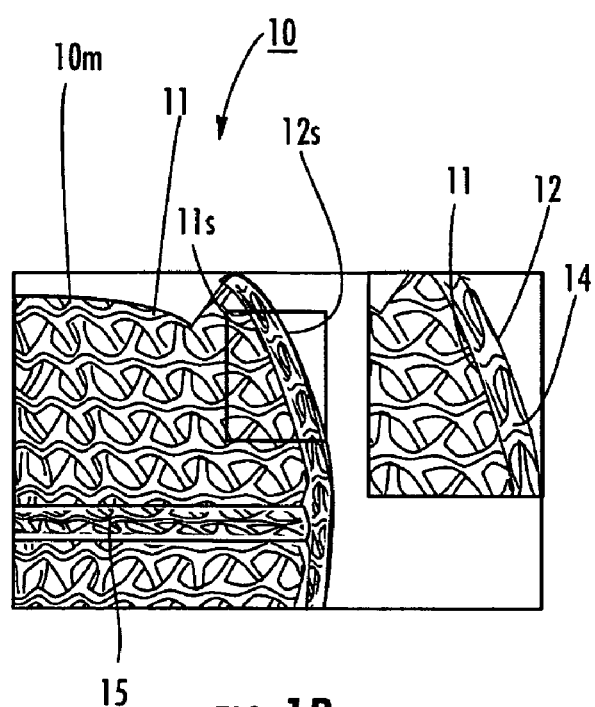
FIG. 1A
FIG. 1B

| MATRIX | SIZE# | AP | AH | WA | KEEL HEIGHT |
|---|---|---|---|---|---|
| S | ED-35101 | 30 | 9 | 6 | 6.75 |
| | ED-35102 | | 11 | 6 | |
| | ED-35103 | | 11 | 10 | |
| | ED-35104 | | 13 | 10 | |
| | ED-35105 | | 13 | 14 | |
| M | ED-35111 | 34 | 9 | 6 | 7.65 |
| | ED-35112 | | 11 | 6 | |
| | ED-35113 | | 13 | 6 | |
| | ED-35114 | | 11 | 10 | |
| | ED-35115 | | 13 | 10 | |
| | ED-35116 | | 15 | 10 | |
| | ED-35117 | | 15 | 14 | |
| L | ED-35121 | 38 | 11 | 6 | 8.55 |
| | ED-35122 | | 13 | 6 | |
| | ED-35123 | | 13 | 10 | |
| | ED-35124 | | 15 | 10 | |
| | ED-35125 | | 15 | 14 | |
| | ED-35126 | | 17 | 14 | |
| XL | ED-35131 | 42 | 11 | 6 | 9.45 |
| | ED-35132 | | 13 | 6 | |
| | ED-35133 | | 13 | 10 | |
| | ED-35134 | | 15 | 10 | |
| | ED-35135 | | 17 | 14 | |

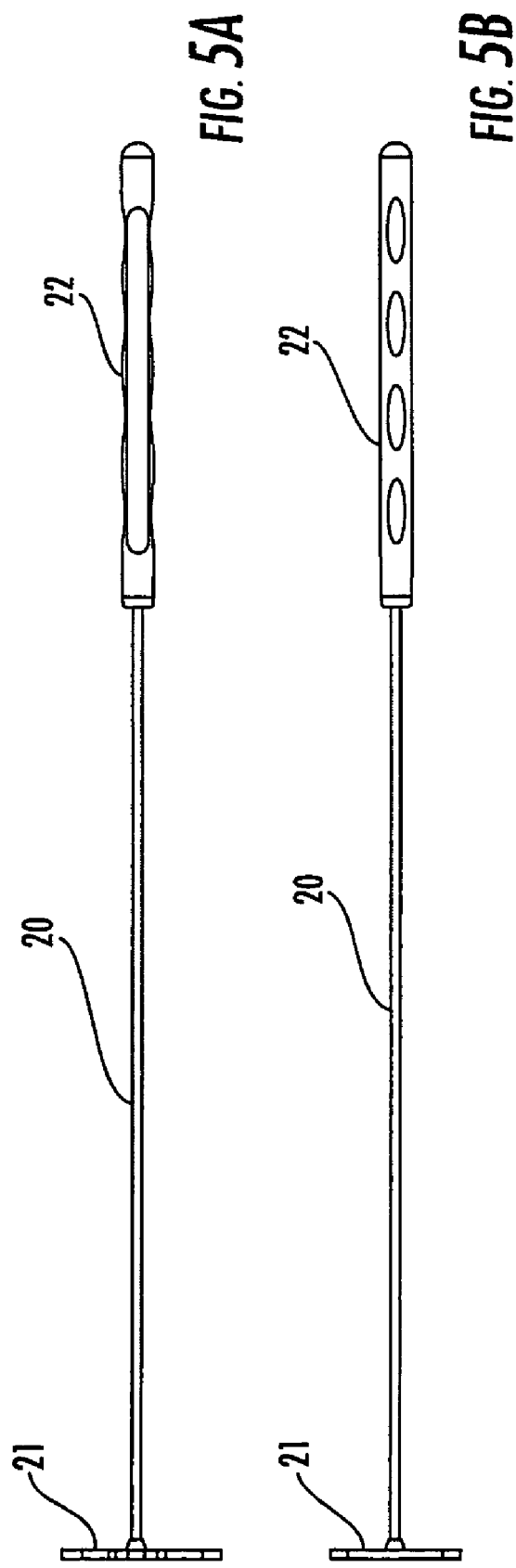

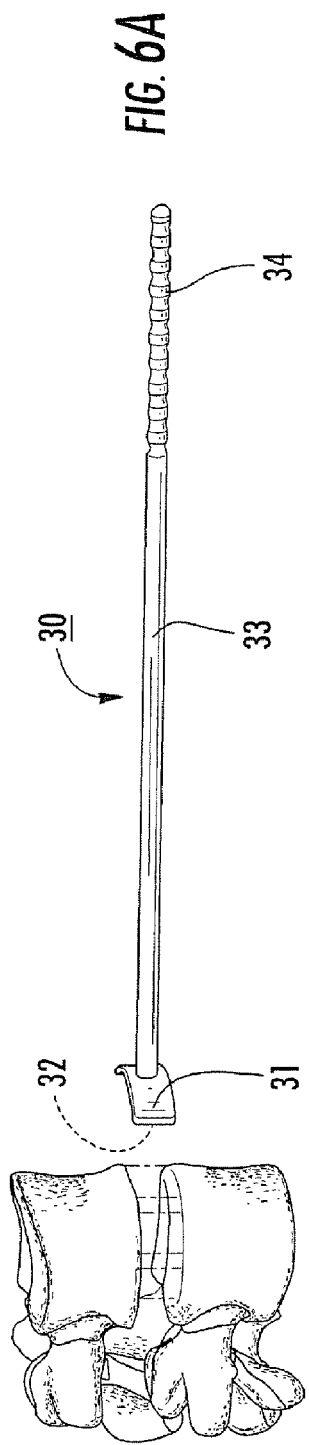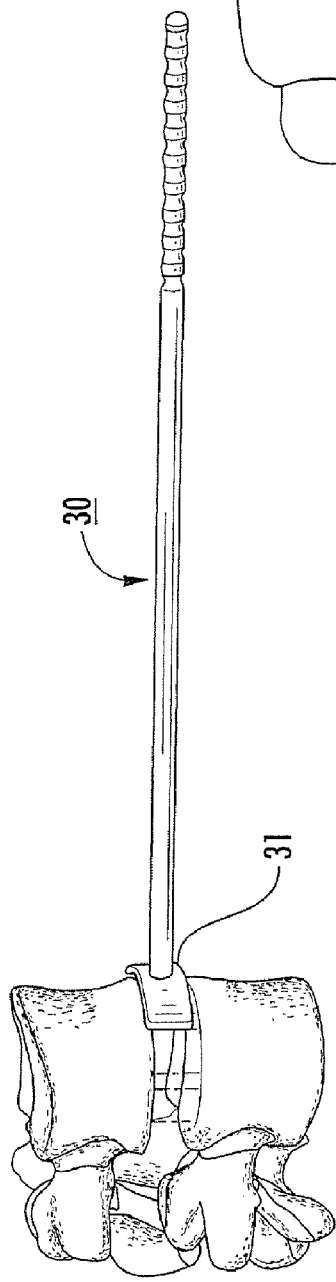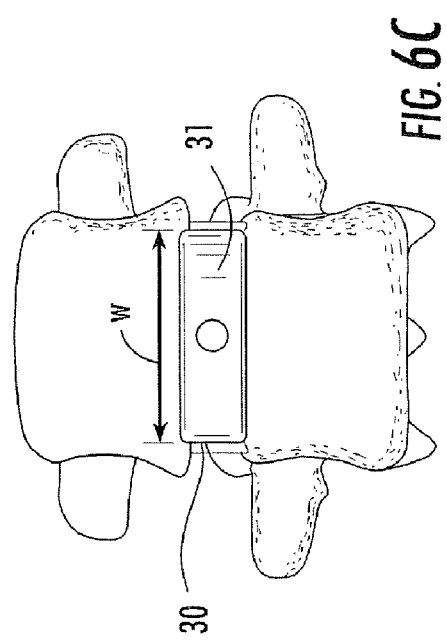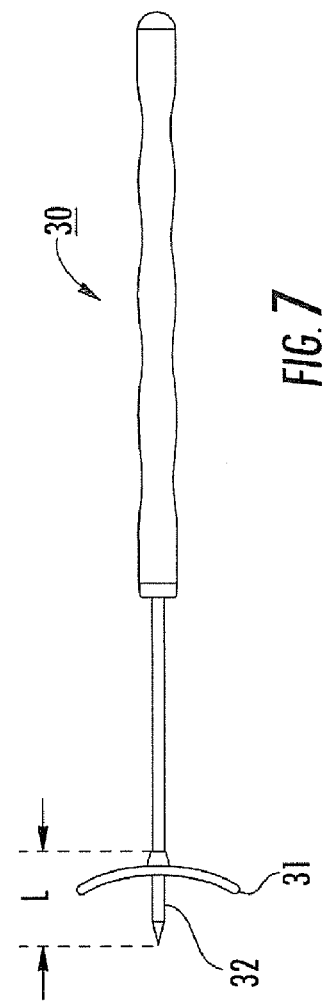
FIG. 6A
FIG. 6B
FIG. 6C
FIG. 7

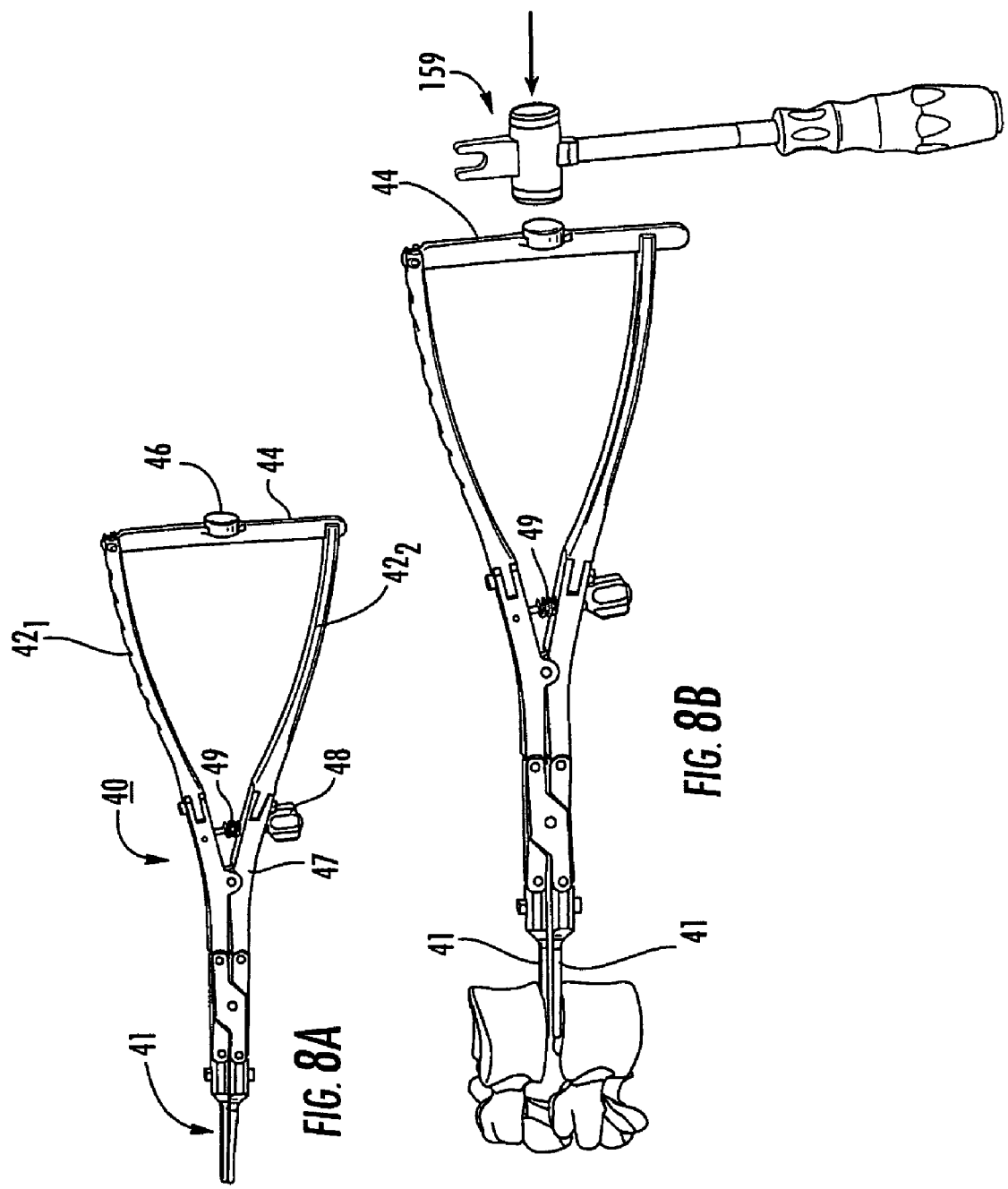
FIG. 8A
FIG. 8B

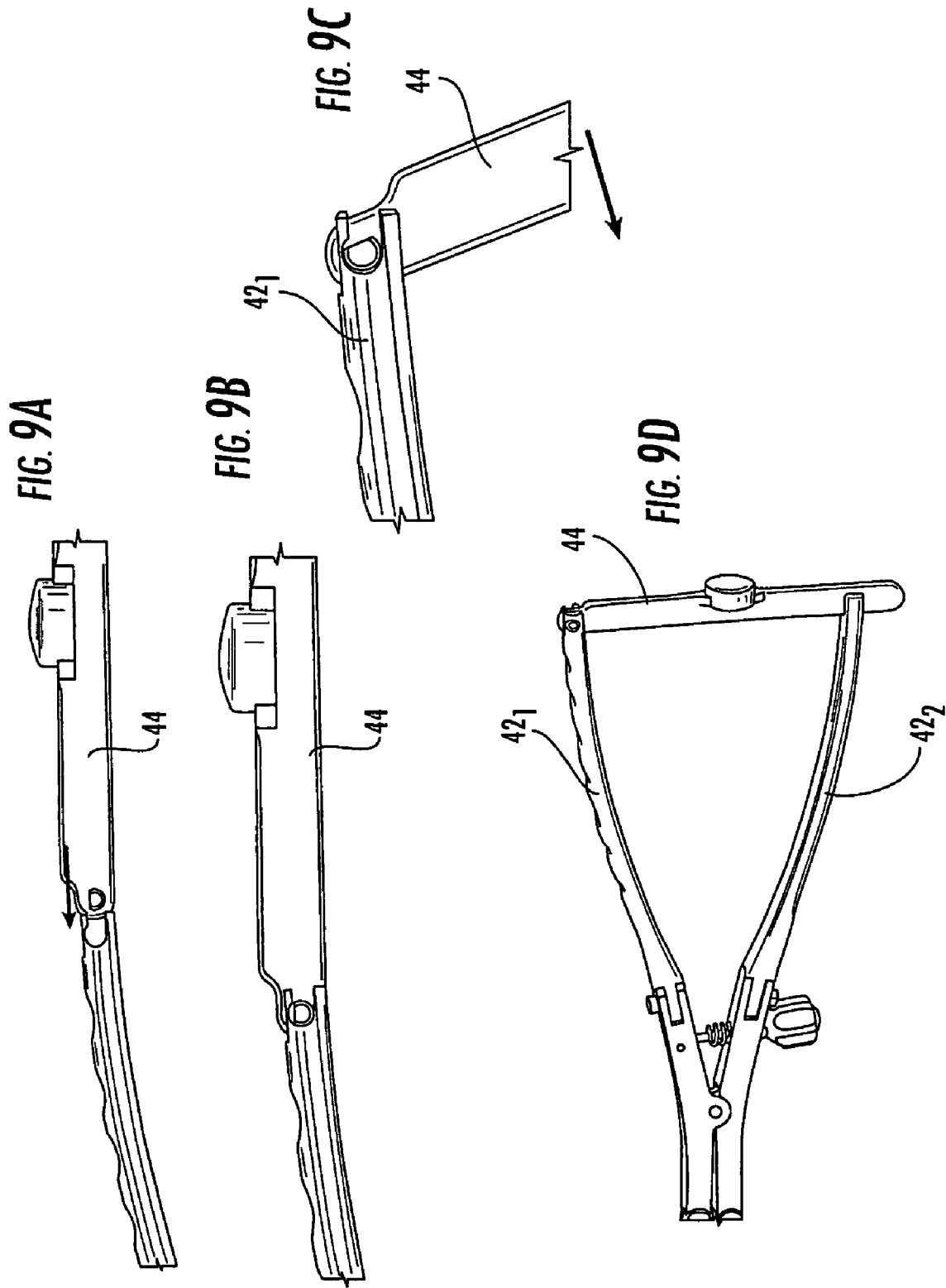

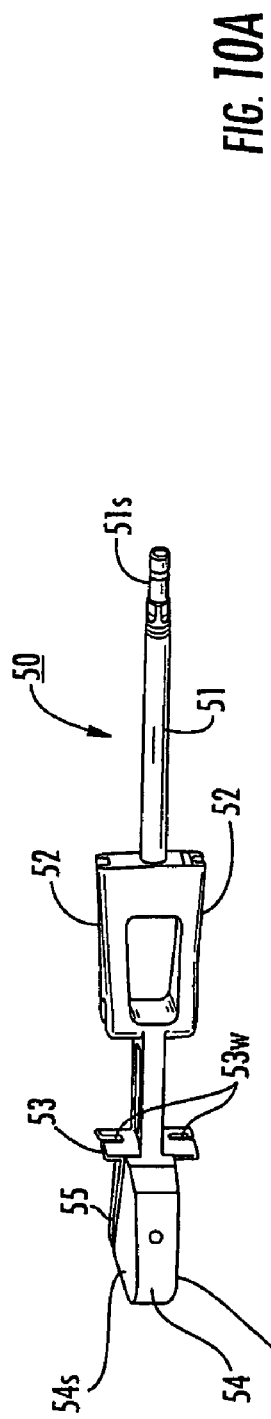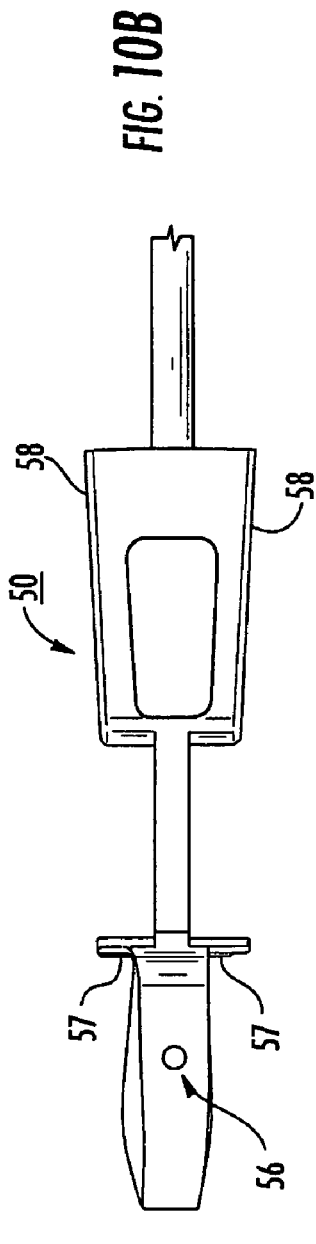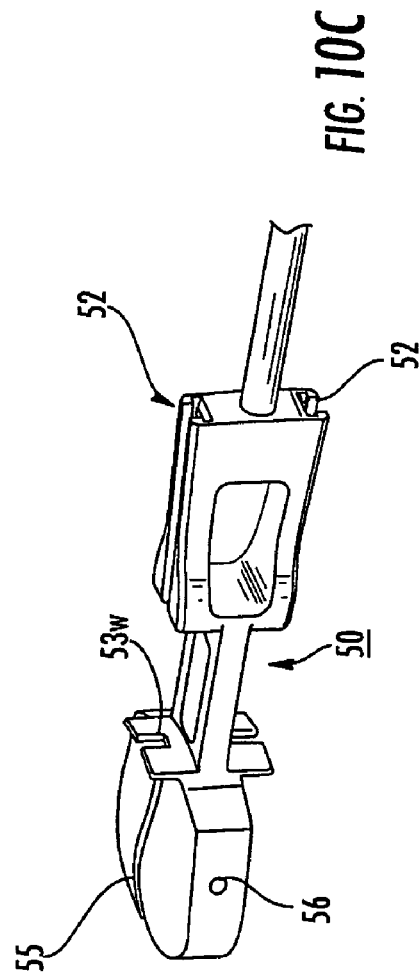
FIG. 10A
FIG. 10B
FIG. 10C

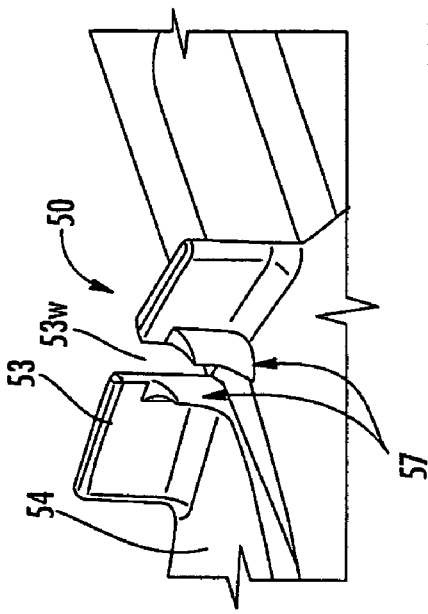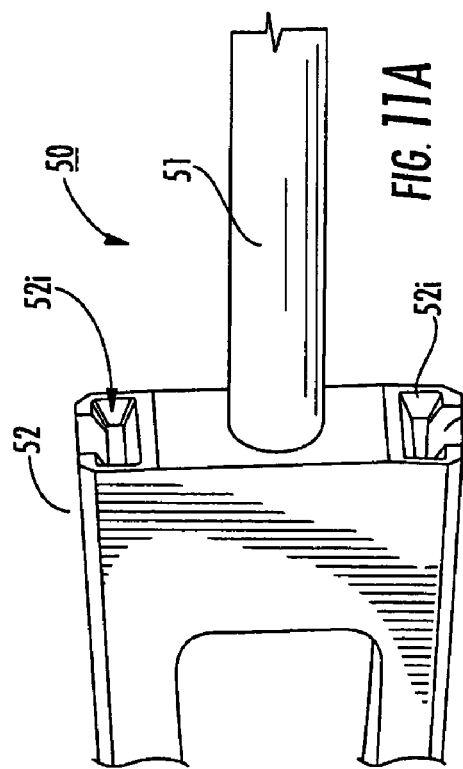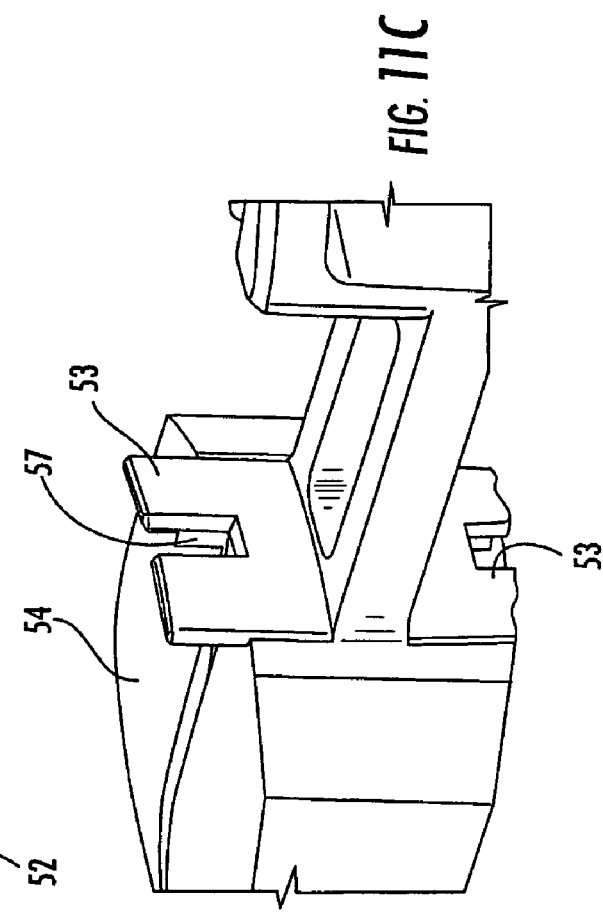

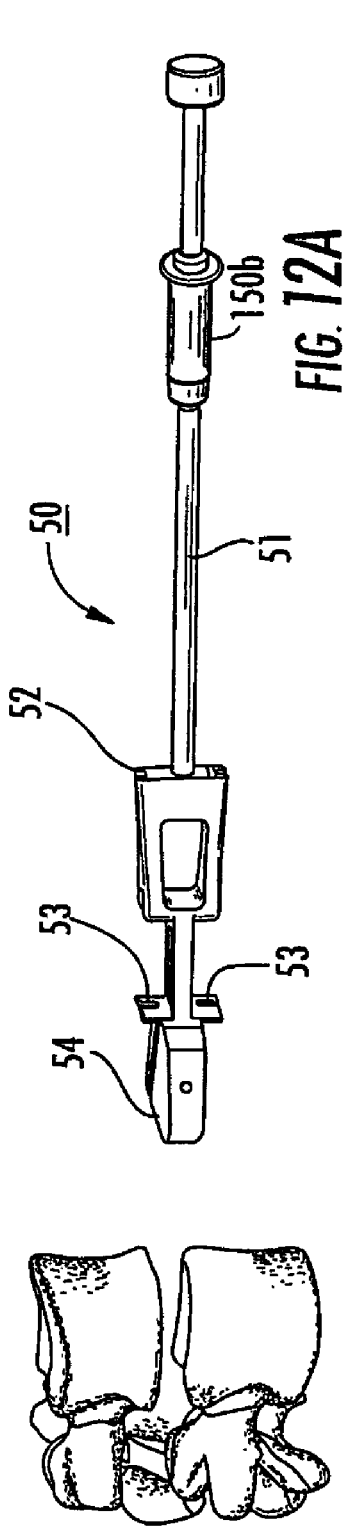
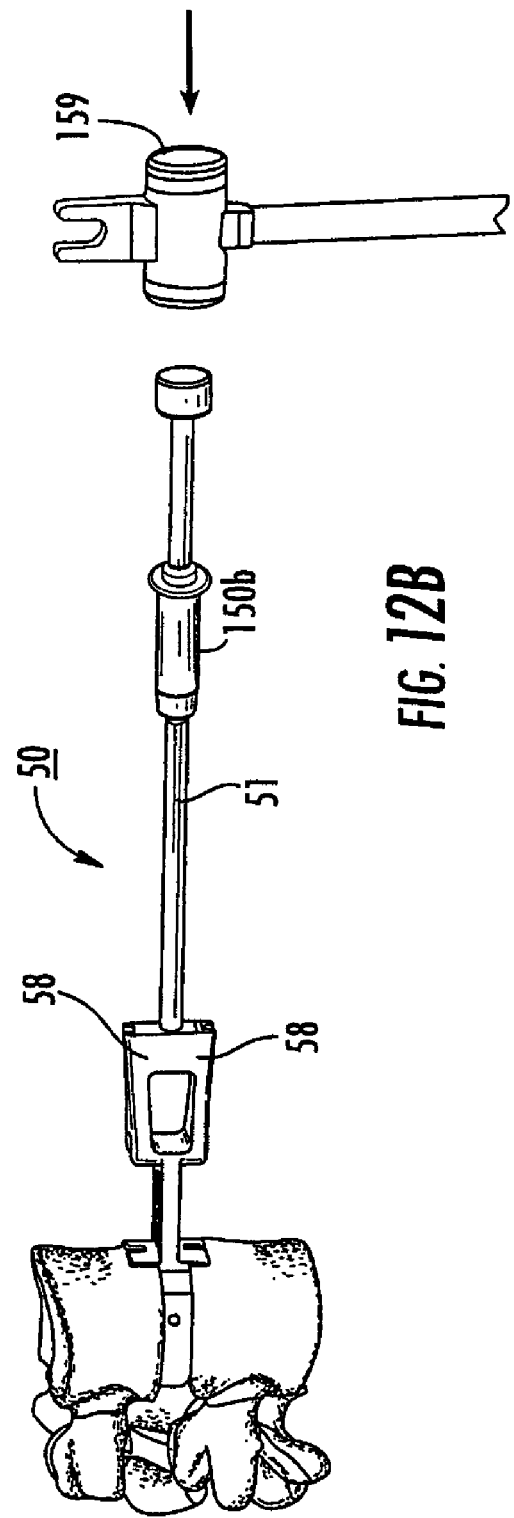
FIG. 12A
FIG. 12B

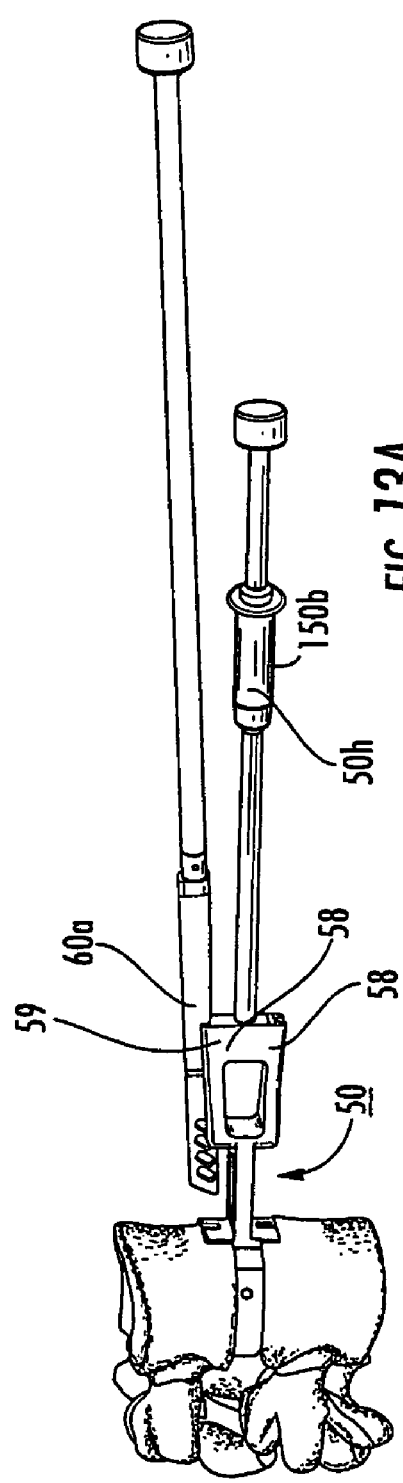
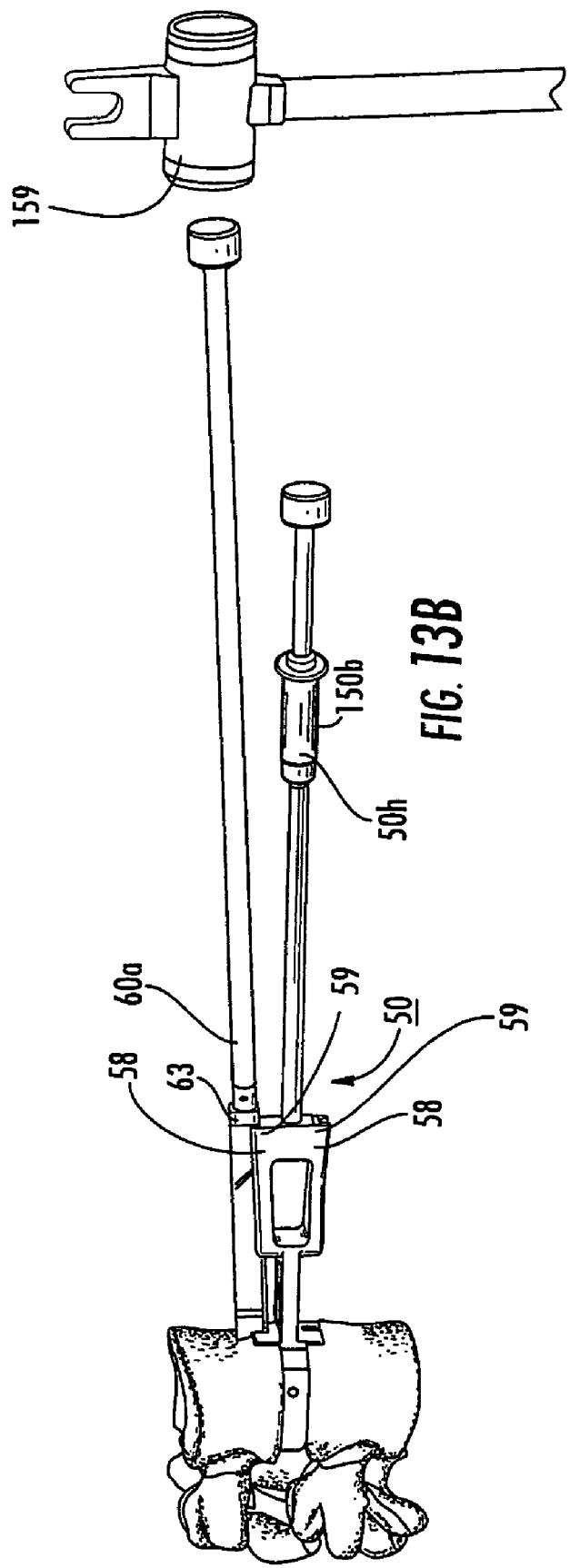
FIG. 13A
FIG. 13B

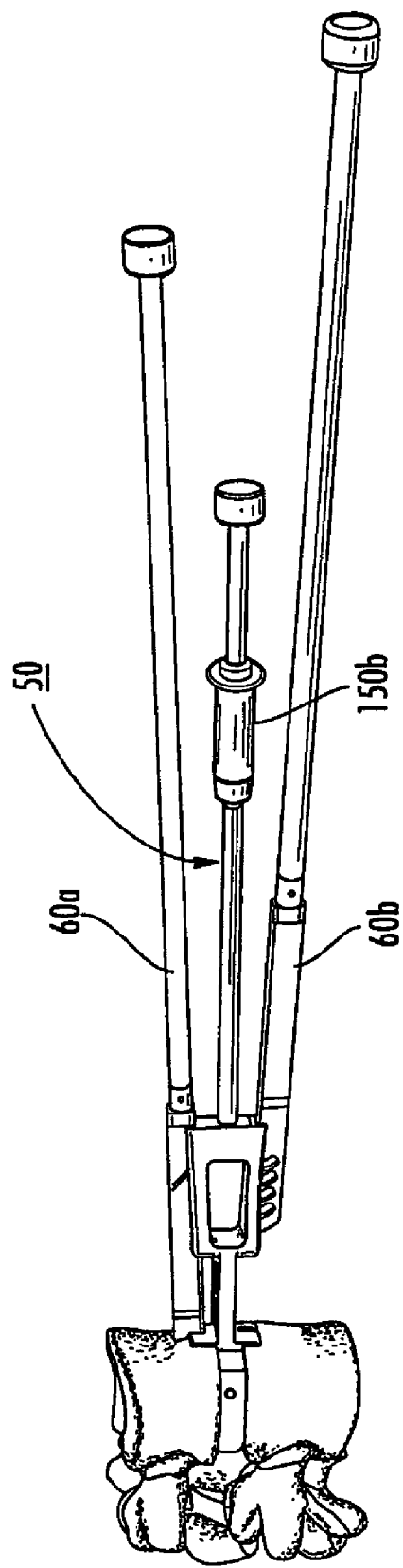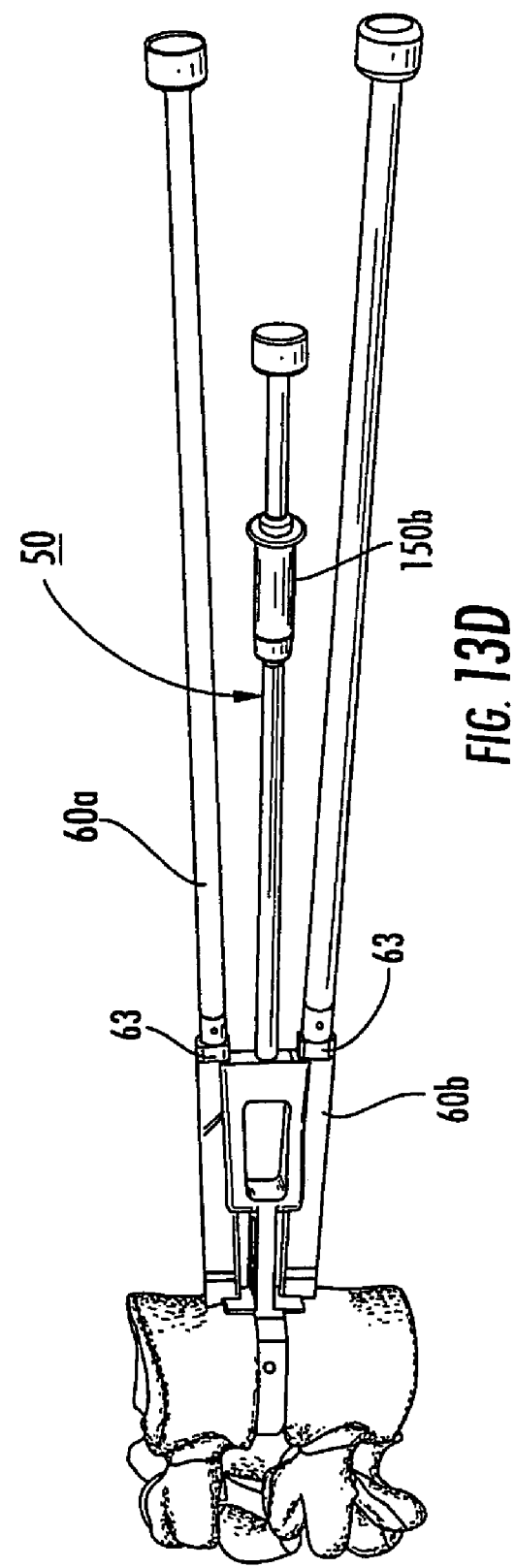

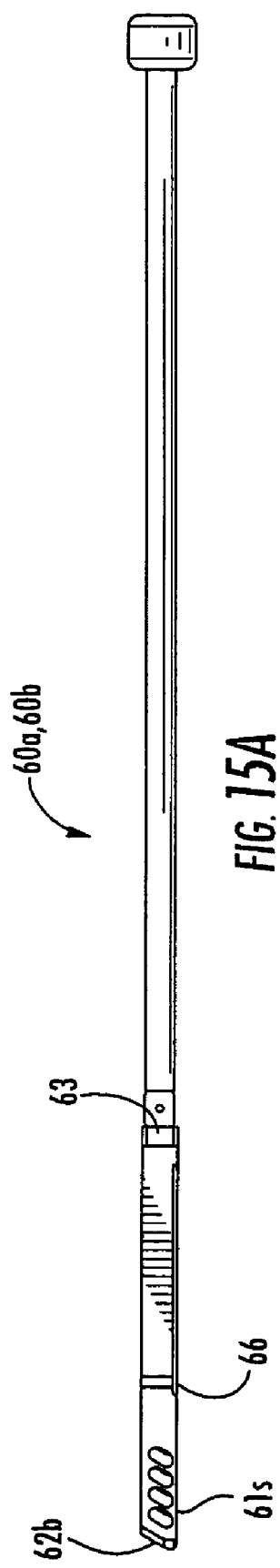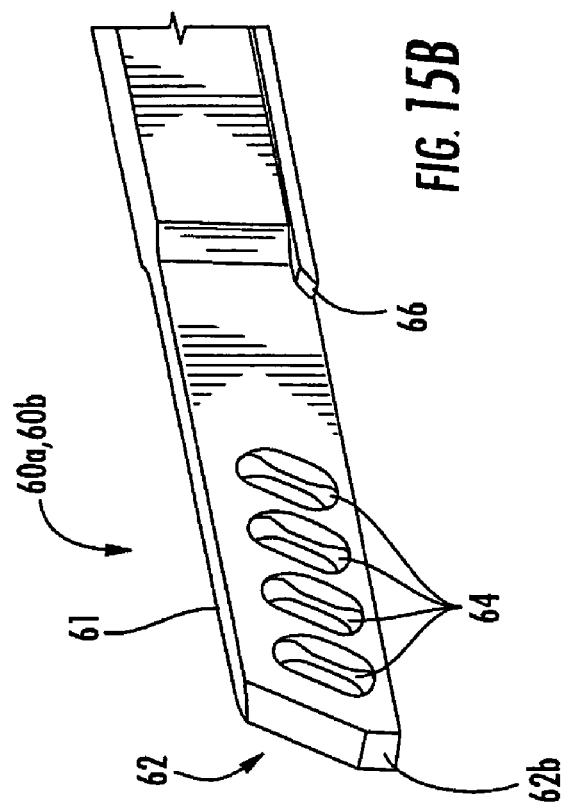

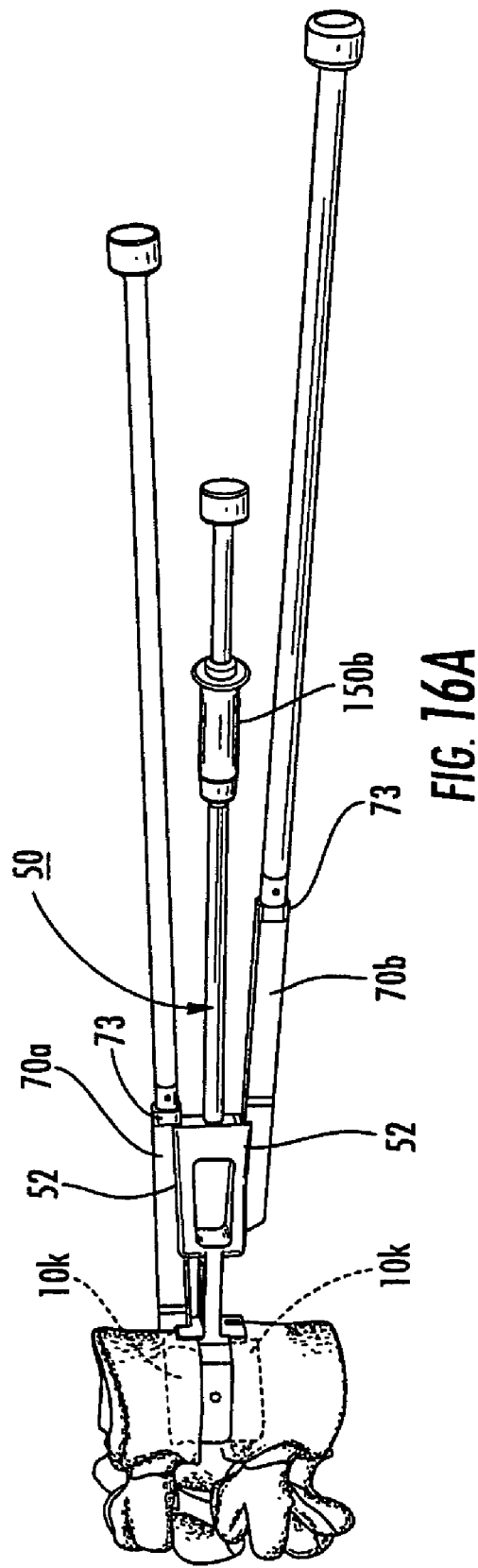

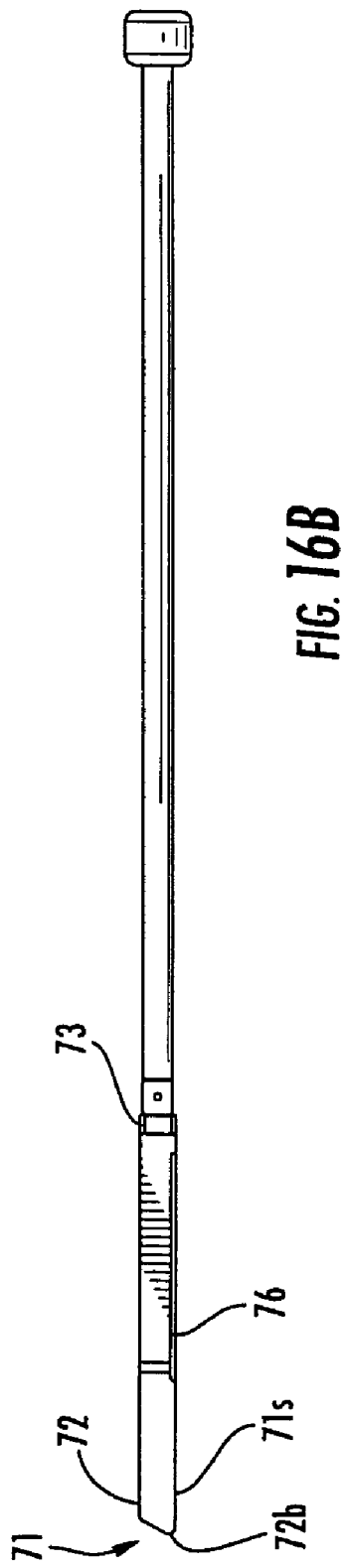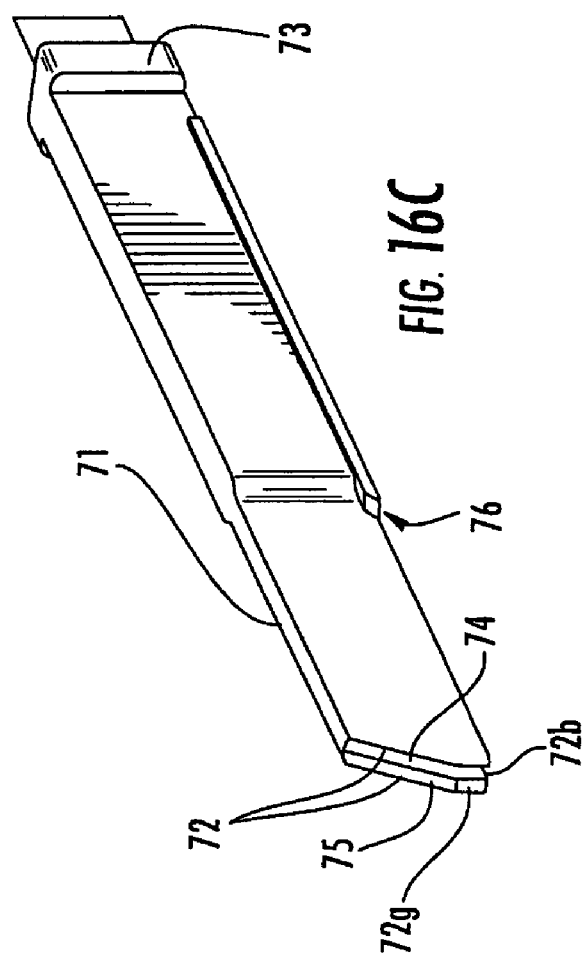
FIG. 16B
FIG. 16C

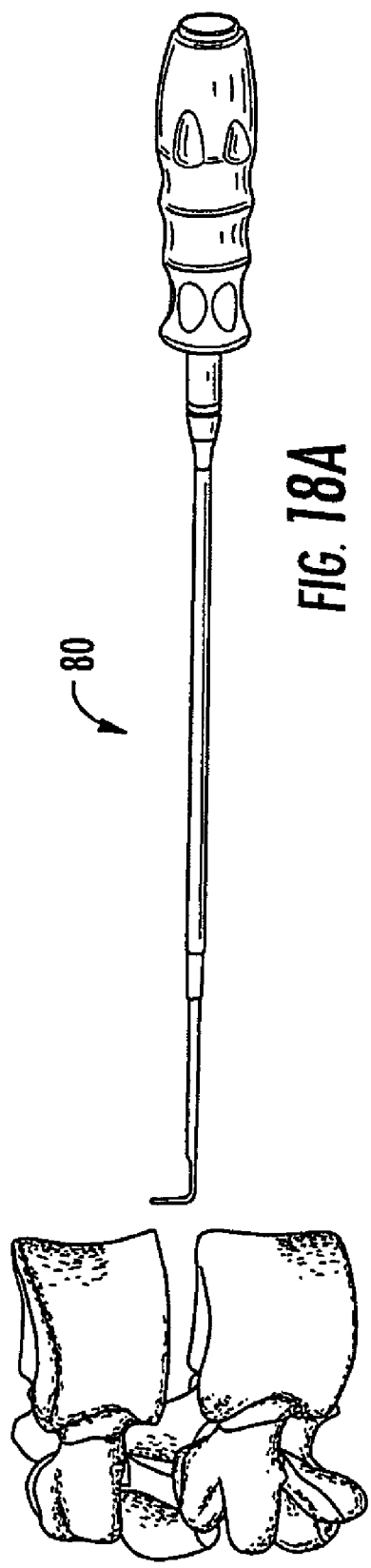
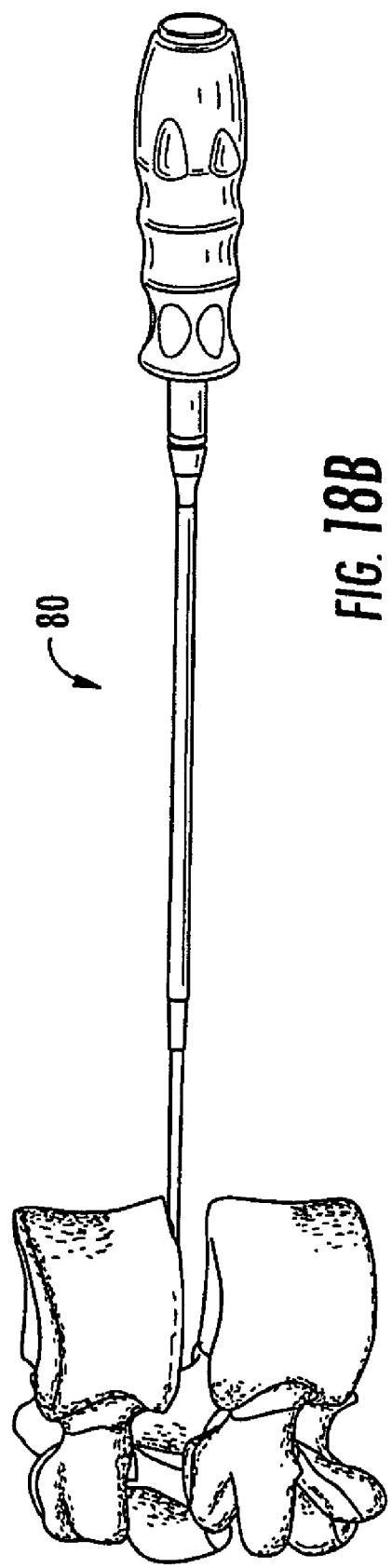

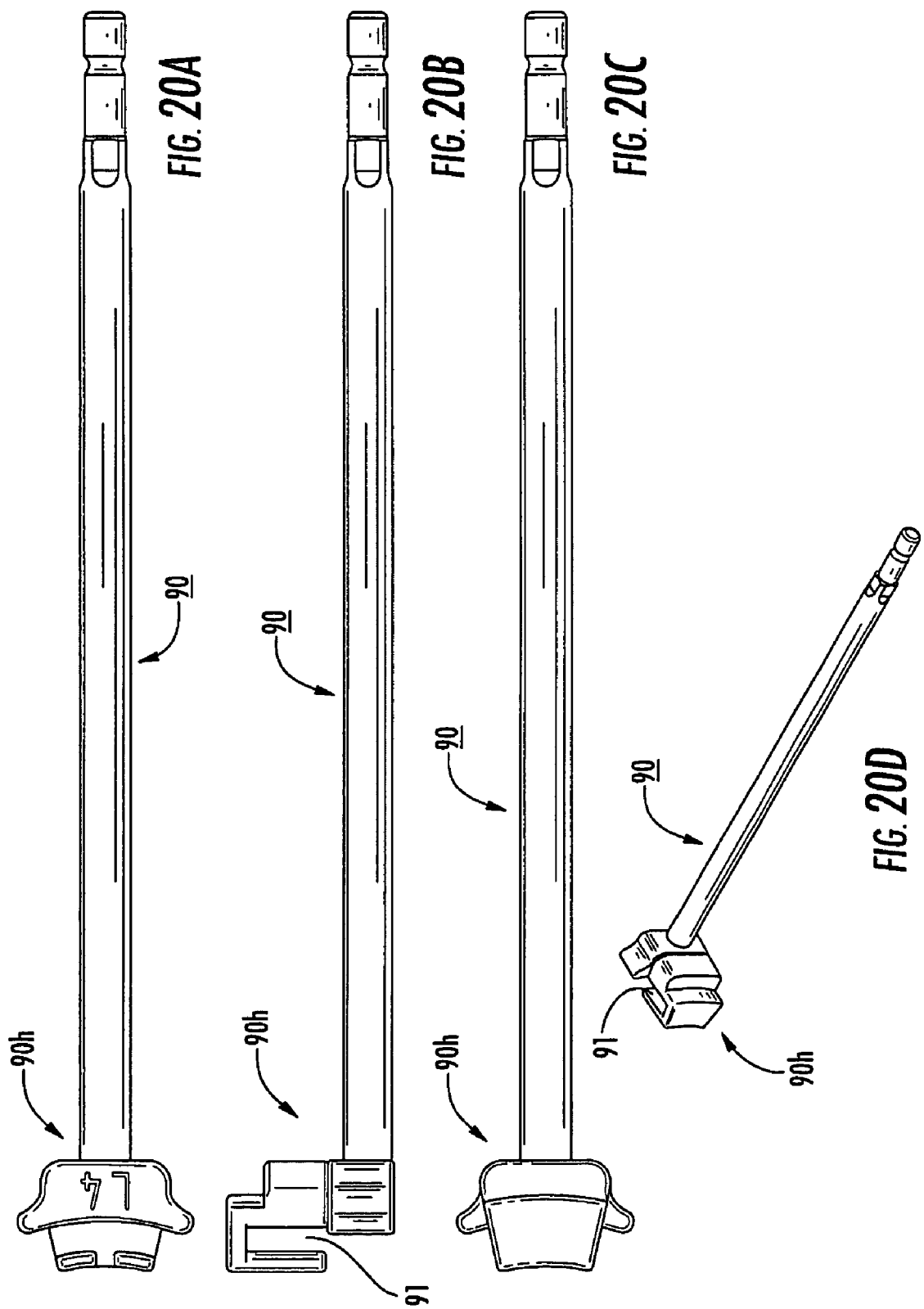

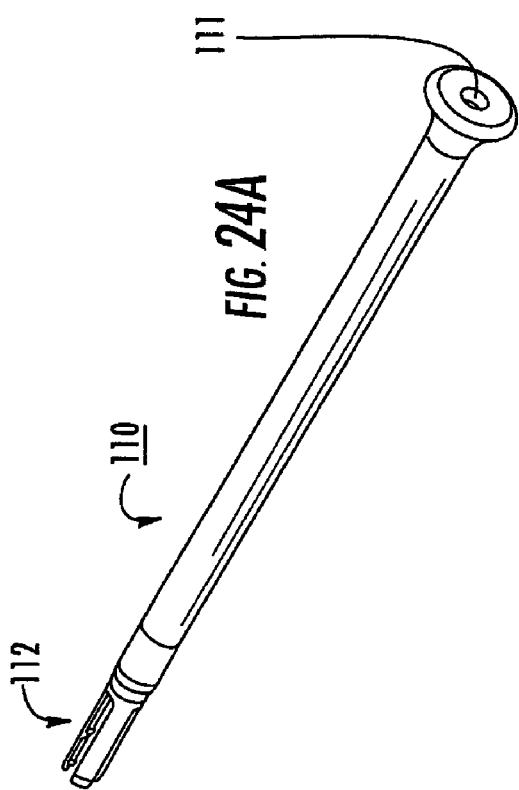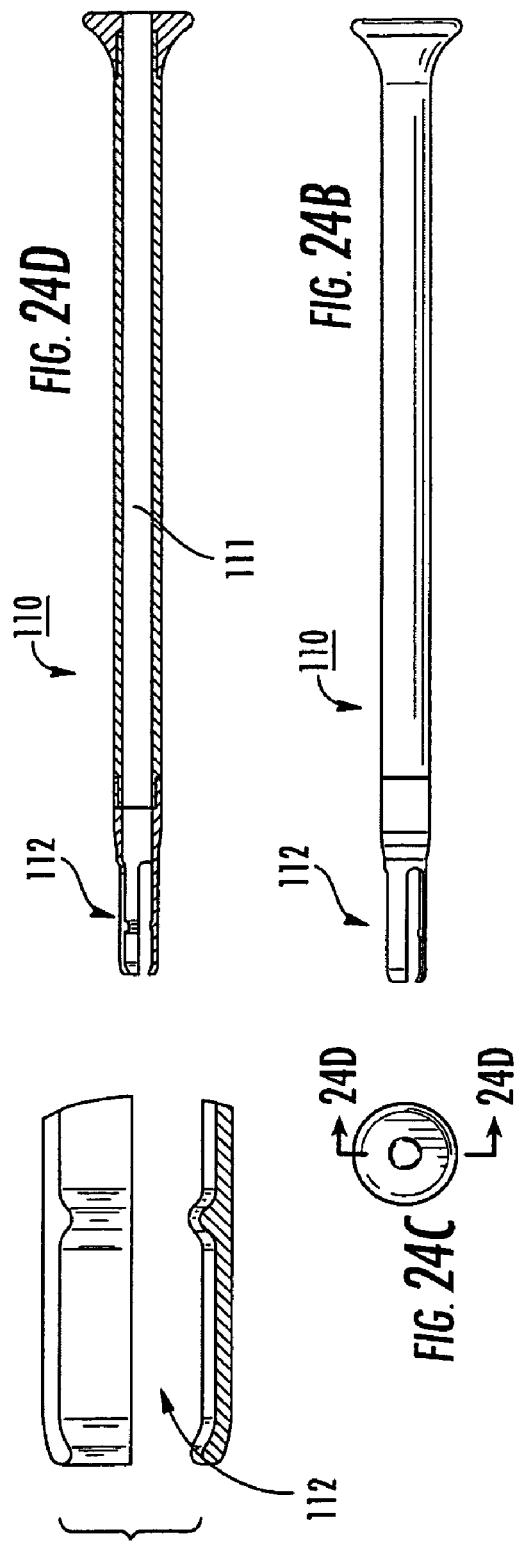

SURGICAL INSTRUMENTS FOR SPINAL DISC IMPLANTS AND RELATED METHODS

RELATED APPLICATIONS

This application claims priority to U.S. Provisional Application Ser. No. 60/914,471, filed Apr. 27, 2007, the entire contents of the above-referenced document is hereby incorporated herein by reference as if recited in full herein.

FIELD OF THE INVENTION

The invention relates to surgical tools for preparing local spinal anatomy and/or placing spinal total disc replacement (TDR) implants.

BACKGROUND OF THE INVENTION

The vertebrate spine is made of bony structures called vertebral bodies that are separated by relatively soft tissue structures called intervertebral discs. The intervertebral disc is commonly referred to as a spinal disc. The spinal disc primarily serves as a mechanical cushion between the vertebral bones, permitting controlled motions between vertebral segments of the axial skeleton. The disc acts as a joint and allows physiologic degrees of flexion, extension, lateral bending, and axial rotation. The disc must have sufficient flexibility to allow these motions and have sufficient mechanical properties to resist the external forces and torsional moments caused by the vertebral bones.

The normal disc is a mixed avascular structure having two vertebral end plates ("end plates"), an annulus fibrosis ("annulus") and a nucleus pulposus ("nucleus"). Typically, about 30-50% of the cross sectional area of the disc corresponds to the nucleus. Generally described, the end plates are composed of thin cartilage overlying a thin layer of hard, cortical bone that attaches to the spongy cancellous bone of the vertebral body. The end plates act to attach adjacent vertebrae to the disc. The annulus of the disc is a relatively tough, outer fibrous ring. For certain discs, particularly for discs at lower lumbar levels, the annulus can be about 10 to 15 millimeters in height and about 10 to 15 millimeters in thickness, recognizing that cervical discs are smaller.

Some recent TDR devices have attempted to allow for motion between the vertebral bodies through articulating implants that allow some relative slippage between parts (e.g., ProDisc®, Charite™), see, for example, U.S. Pat. Nos. 5,314,477, 4,759,766, 5,401,269 and 5,556,431. As an alternative to the metallic-plate, multi-component TDR (total disc replacement) designs, a flexible solid elastomeric spinal disc implant that is configured to simulate natural disc action (i.e., can provide shock absorption and elastic tensile and compressive deformation) is described in U.S. Patent Application Publication No. 2005/0055099 to Ku, the contents of which are hereby incorporated by reference as if recited in full herein.

SUMMARY OF EMBODIMENTS OF THE INVENTION

Embodiments of the invention are directed to surgical instruments for preparing target spinal structure and/or for placing spinal implants.

Some embodiments are directed to trials for spinal surgery. The trials include: (a) a trial implant portion having a shape corresponding to an implantable spinal disc implant; (b) a shaft connected to the trial implant portion; and (c) at least one axially extending cutting guide attached to the shaft at a position that is axially spaced apart from the trial implant portion, the cutting guide slot configured to releasably slidably receive and guide a cutting member toward vertebral bone.

The at least one cutting guide can comprise an axially extending slot residing in a ramp extending toward the trial implant portion. The trial implant can have superior and inferior bearing surfaces that are devoid of cutting guide slots.

The at least one cutting guide can be two cutting guides: a superior cutting guide and an inferior cutting guide. Each cutting guide can have a respective cutting guide slot. The trial can also include an upper and lower trial implant portion stop with a respective alignment window residing respectively above and below the bearing surfaces on an anterior side of the trial implant portion. The upper and lower alignment windows are configured to allow cutting members to extend therethrough while held in a desired orientation by the corresponding superior and inferior cutting guide slot.

The trial can include a shallow groove on the superior and inferior bearing surfaces of the trial implant portion, the shallow groove configured so as to avoid contact with the cutting blade during formation of a keelway.

Other embodiments are directed to trials in combination with a pair of universal reamers and a pair of universal chisels. The at least one cutting guide can be two cutting guides, one for directing one of the reamers and chisels to form a superior keelway and the other for directing the other one of the reamers and chisels to form an inferior keelway. The reamers and the chisels are cutting members that releasably and slidably engage the cutting guides.

Still other embodiments are directed to sets of trials for preparing an intervertebral space for spinal implants. Each of the trials includes: (a) a trial implant portion with superior and inferior vertebral bone bearing surfaces; (b) a superior ramp with a cutting guide slot that declines in a direction toward the trial implant portion; (c) an inferior ramp with a cutting guide slot that inclines in a direction toward the trial implant portion; and (d) a cutting window residing between the trial implant portion and the superior and inferior ramps. Different ones of the trial implant portions have at least one of the following: (a) different anterior heights; (b) different wedge angles; (c) different antero-posterior diameters; and (d) different lengths from a proximal side of the ramp to an anterior stop of the trial thereby allowing the use of a common reamer and/or chisel for each of the various trials.

Yet other embodiments are directed to inserters configured to releasably hold a spinal implant during surgical placement into position in the spine. The inserters include an inserter head configured to engage a skirt of a unitary non-articulating spinal implant and allow a primary portion of the implant body to project outwardly therefrom with superior and inferior keels thereon exposed for implantation into keelways in vertebral bone.

In particular embodiments, the inserter is in combination with a spinal implant. The spinal implant can have a skirt comprising mesh that engages an anterior side of a target vertebral body anterior surface. The spinal implant may have superior and inferior flexible keels that are moldably attached to a body of crystalline PVA hydrogel that forms a body of the implant.

Still other embodiments are directed to pilot hole punches for spinal surgeries. The punches include: (a) a shaft; (b) a punch attached to the shaft, the punch residing at a forwardmost end of the shaft, wherein the punch has a penetrating length sufficient to extend through a skirt of an implant and through anterior cortical bone; and (c) a punch stop residing proximate the punch to inhibit the punch from penetrating more than about 3-10 mm, thereby preventing over-insertion into the vertebral bone posteriorly.

Some embodiments are directed to spinal keelway clearing hooks comprising a planar forward end with rounded edges attached to an axially extending shaft, wherein the planar forward end extends substantially orthogonal to the shaft.

Still other embodiments are directed to distractors that include: (a) a pair of parallel distracting blades; (b) a distractor body attached to the blades; and (c) a pair of handles attached to the distractor body; and (d) a bridge that releasably slidably engages each of the handles.

Yet other embodiments are directed to methods of forming keelways in vertebral bodies. The methods include: (a) inserting a trial with a superior and inferior cutting guide; (b) inserting a first chisel into one of the superior or inferior cutting guides and into vertebral bone to form a superior keelway; and (c) inserting a second chisel into the other cutting guide while the first chisel remains in the superior keelway to form an inferior keelway.

The methods may also include: (d) removing one of the first and second chisels from the cutting guide to form an open cutting guide, leaving the other chisel in position; (e) inserting a first reamer into the open cutting guide and into the associated keelway; (f) removing the chisel from the cutting guide to form an open cutting guide, while the first reamer remains in position; (g) inserting a second reamer into the open cutting guide and into the associated keelway; and (h) removing the first and second reamers.

Other embodiments are directed to methods of implanting a spinal implant. The methods include: (a) releaseably engaging a non-articulating spinal implant with a skirt with an inserter so that a primary portion of the implant body projects outwardly therefrom with superior and inferior keels thereon exposed for implantation into keelways in vertebral bone; (b) inserting the spinal implant into a target intervertebral disc space to force adjacent vertebral bones further apart to perform a supplemental distraction and to place the keels in a respective keelway in the vertebral bone with the skirt residing against a surface of anterior vertebral bone; (c) releasing the inserter; (d) punching a plurality of apertures through the skirt of the implant and through underlying anterior cortical bone; and (e) inserting screws into the apertures to affix the skirt to the vertebral bone.

Yet other embodiments are directed to surgical instrument sets for spinal surgeries. The surgical instrument sets include: (a) a pilot hole punch; (b) a keelway clearing hook; (c) a set of trials; and (d) a set of spinal implants.

The surgical instrument sets may also include one or more of the following: a pair of chisels that cooperate with the trials; a pair of reamers that cooperate with the trials; an inserter; a screwdriver; a screw holder configured to releasably engage the screw driver and positively hold a target screw during insertion; a plurality of screws; a plurality of access window tools; a plurality of discectomy width templates; a pusher; a mallet, a reamer cleaning tool and a distractor. Some of the tools can be pre-arranged in subsets of tools according to size.

Other embodiments are directed to medical spinal surgical instrument kits. The kits can be provided as a first universal tool tray with universal tools comprising a distractor, a pair of reamers, a pair of chisels, a pilot hole punch, a screw driver and screw holder (and, optionally, implant anchoring screws), and can include a pusher. The kits can also be provided with a second "size" specific tray with correspondingly sized tools in small, medium, large and extra large arrangements. The second tray of size-specific tools can include trials, spinal implants, at least one inserter and an access window tool, and/or a discectomy width template.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 5A is a top view of an access window tool according to embodiments of the present invention.

FIG. 5B is a side view of the tool shown in FIG. 5A.

FIGS. 6A and 6B are side perspective views of a Discectomy Width Template (DWT) according to embodiments of the present invention.

FIG. 6C is an end view of a DWT according to embodiments of the present invention.

FIG. 7 is a top view of a DWT according to some embodiments of the present invention.

FIGS. 8A and 8B are side views of a distractor according to embodiments of the present invention.

FIGS. 9A-9C are enlarged partial views of the device shown in FIGS. 8A and 8B illustrating assembly of a bridge to a handle, then pivoting of the assembled bridge downwardly according to some embodiments of the present invention.

FIG. 9D is a partial side view of the device shown in FIGS. 8A and 8B illustrating the bridge shown in FIGS. 9A-9C being slidably connected to the other handle according to some embodiments of the present invention.

FIG. 10A is a side perspective view of a trial according to embodiments of the present invention.

FIG. 10B is an enlarged partial side view of the device shown in FIG. 10A.

FIG. 10C is an enlarged partial side perspective view of the device shown in FIG. 10A.

FIG. 11A is a greatly enlarged partial rear side perspective view of the device shown in FIG. 10A illustrating cutting guide channels/slots according to some embodiments of the present invention.

FIG. 11B is a greatly enlarged partial end perspective view of the device shown in FIG. 10A illustrating anterior extending anchoring members according to embodiments of the present invention.

FIG. 11C is a greatly enlarged partial side perspective view of the device shown in FIG. 10A illustrating a cutting blade window according to embodiments of the present invention.

FIGS. 12A and 12B are side perspective views of the trial being positioned in a target intervertebral space according to embodiments of the present invention.

FIGS. 13A-13D are side perspective views of serial operations that can be used to cut keelways using the trial according to embodiments of the present invention.

FIG. 15A is a side perspective view of a cutter or chisel according to some embodiments of the present invention.

FIG. 15B is a greatly enlarged partial end perspective view of the device shown in FIG. 15A.

FIG. 16A is a side perspective view of ream cutters cooperating with the trial.

FIG. 16B is a side view of a ream cutter according to embodiments of the present invention.

FIG. 16C is an enlarged partial side end perspective view of the ream cutter shown in FIG. 16B.

FIGS. 18A and 18B are side perspective views of a keelway cleaner (hook) according to embodiments of the present invention.

FIG. 20A is a top view of an inserter configured to releasably hold a spinal implant according to embodiments of the present invention.

FIG. 20B is a side view of the device shown in FIG. 20A.

FIG. 20C is a bottom view of the device shown in FIG. 20A.

FIG. 20D is a side perspective view of the inserter shown in FIG. 20A.

FIG. 24A is a side perspective view of a hex screw holder according to embodiments of the present invention.

FIG. 24B is a side view of the device shown in FIG. 24A.

FIG. 24C is an end view of the device shown in FIG. 24B.

FIG. 24D is a section view taken along line 24D-24D in FIG. 24C.

FIG. 24E is an enlarged partial sectional end view of the device shown in FIG. 24D.

DETAILED DESCRIPTION

Figure 1:
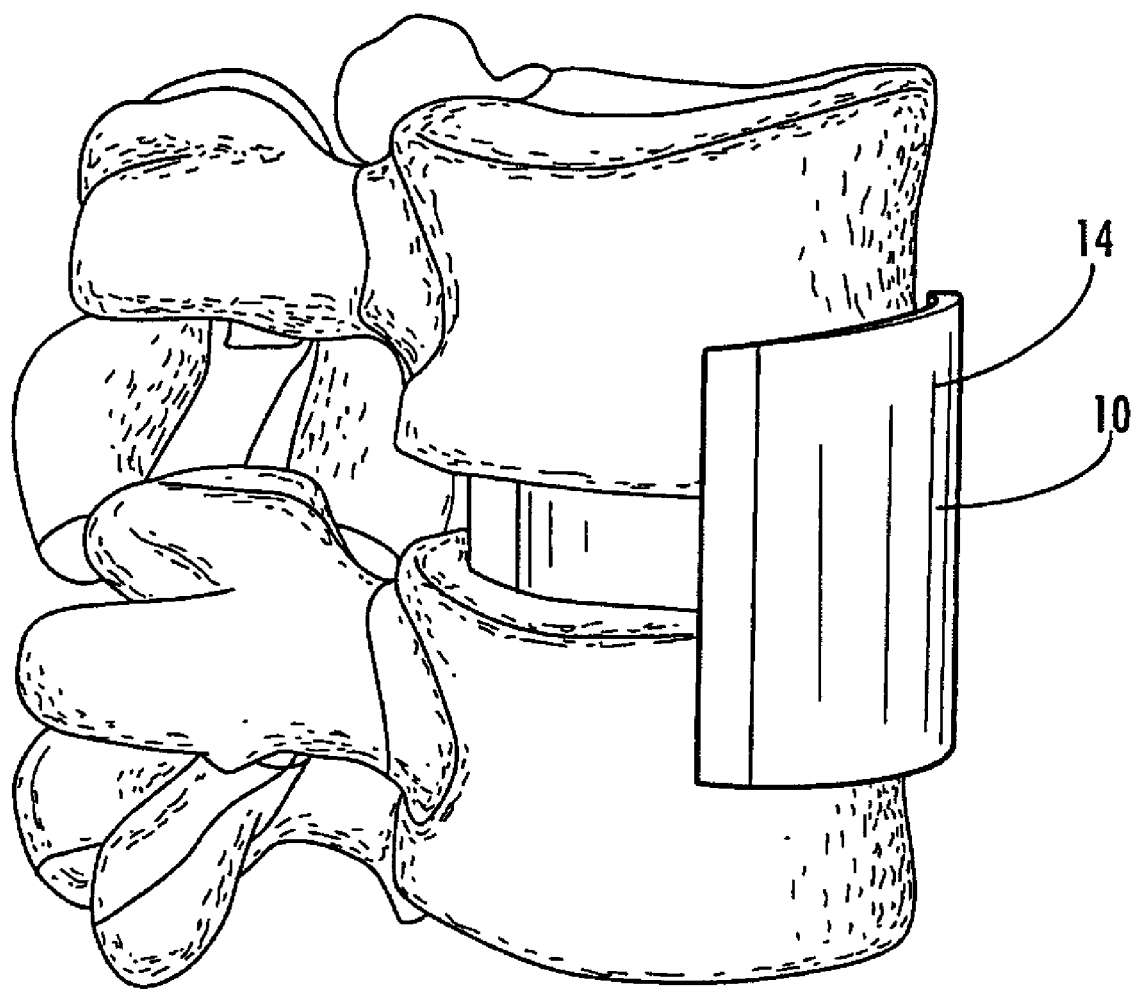
FIG. 1 is a side perspective view of a spinal implant according to some embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "spinal disc implant" and "spinal disc prosthesis" are used interchangeably herein to designate total disc replacements using an implantable total spinal disc replacement prosthesis (rather than a nucleus only) and as such are configured to replace the natural spinal disc of a mammalian subject (for veterinary or medical (human) applications).

The term "flexible" means that the member can be flexed or bent. In some embodiments, the keel is flexible but has sufficient rigidity to be substantially self-supporting so as to be able to substantially maintain a desired configuration outside of the body. The keel can include reinforcement to increase its rigidity.

The term "keel" means an implant component, feature or member that is configured to be received in a recess or mortise in an adjacent bone to facilitate short and/or long-term fixation and/or to provide twist or torsion resistance in situ.

The term "mesh" means any flexible material in any form including, for example, knotted, braided, extruded, stamped, knitted, woven or otherwise, and may include a material with a substantially regular foramination pattern and/or irregular foramination patterns.

The term "macropores" refers to apertures having at least about a 0.5 mm diameter or width size, typically a diameter or width that is between about 1 mm to about 3 mm, and more typically a diameter or width that is between about 1 mm to about 1.5 mm (the width dimension referring to non-circular apertures). Where mesh keels are used, the macropores are larger than the openings or foramina of the mesh substrate. The macropores may promote bony through-growth for increased fixation and/or stabilization over time.

The term "loop" refers to a keel shape in the affected material that has a closed or nearly closed turn or figure. For example, the loop can have its uppermost portion merge into two contacting lower portions or into two proximately spaced apart lower portions. The term "fold" means to bend over and the bend of the fold may have a sharp or rounded edge. The terms "pleat" or "fold" refer to doubling material on itself (with or without sharp edges).

The term "universal" means that the so-called tool or component thereof can be used with all of the different sized trials or different sized implants, not requiring any trial specific and/or implant specific component.

Figure 2A:
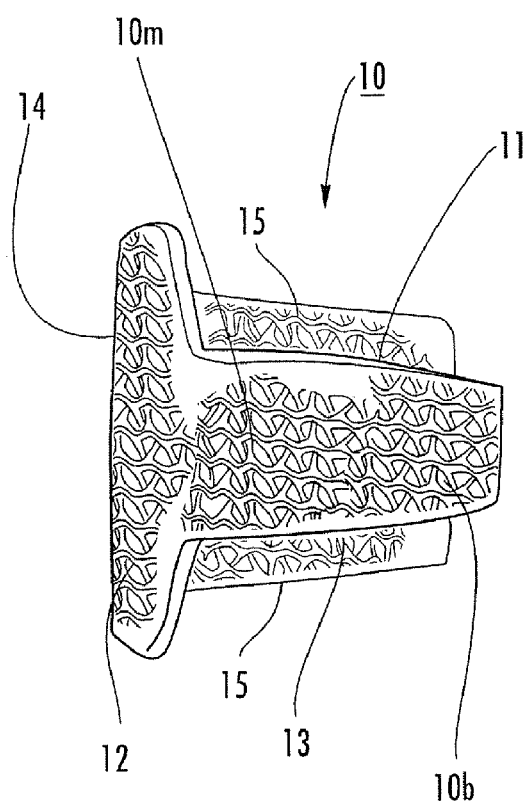
FIG. 2A is a side view of an implantable spinal disc prosthesis with keels and a skirt according to embodiments of the invention.
Figure 2B:
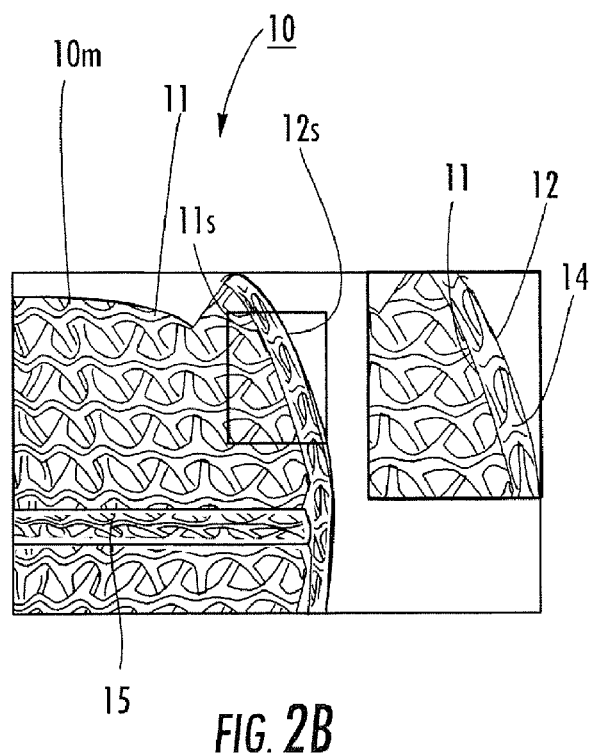
FIG. 2B is a partial enlarged top view of the device shown in FIG. 2A.

FIG. 1 illustrates one embodiment of spinal disc implant 10. As shown in FIGS. 2A and 2B, the implant 10 includes at least one keel 15 on each of the upper and lower primary surfaces. Other keel orientations and configurations may also be used. The keel 15 can extend a distance outward from the implant body between about 2 to about 15 mm, typically between about 6-10 mm. The keel 15 may be flexible and can provide twist or torsion resistance for the implant 10 and/or facilitate short and long term fixation. In some embodiments, the keel 15 can comprise a mesh fabric material with a thickness between about 0.1-5 mm, typically between about 0.5-3 mm, and more typically between about 1-2 mm. The flexible keel 15 can include structural reinforcement, such as, for example, coatings, materials or components that add rigidity to the keel 15. In some particular embodiments, the keel 15 is at least partially embedded with crystalline PVA hydrogel to add thickness and rigidity. The flexible keels 15 can comprise a biocompatible mesh material such as a polyester fabric and the TDR spinal implants may further comprise a crystalline poly(vinyl alcohol) (PVA) hydrogel. The flexible keels can be configured to bend (slightly) and/or move side-to-side while having sufficient rigidity to maintain a generally upwardly or downwardly extending orientation outside the body. For additional description of an exemplary spinal disc implant with a flexible keel, see, co-pending, co-assigned U.S. patent application Ser. No. 11/626,401, the contents of which are hereby incorporated by reference as if recited in full herein.

The keel 15 is configured to enter a respective channel or mortise formed in an adjacent vertebrae. In some embodiments, the keel 15 is cut part way through in the anterior-posterior direction. The channel can have a relatively shallow depth that is greater than the height of the keel 15. In some embodiments, the channel can have a depth that is between about 5-12 mm. In some embodiments, the implant 10 is substantially covered with at least partially embedded mesh layers and the keel 15 is defined by an outwardly extending looped and/or fold of a mesh layer. The mesh layers can be polyester mesh layers that may be extruded, knitted, braided, woven or otherwise formed into a mesh pattern. In some embodiments, the mesh comprises a multi-filament fiber(s) that can provide increased strength over conventional polyester material, such as, for example, a polyester mesh multifilament fiber that, for example, can be made out of a High Tenacity Polyester Teraphthalate (HTPET), which typically has a longer molecular chain than conventional polyester material, therefore providing more strength to the mesh than a regular polyester material. In some embodiments, the mesh can be a high strength mesh that using a ball burst test (ref. ASTM D3787-01) can have a burst value between about 1500-3000N and also a slope of the linear portion of the load/displacement curve of between about 150-300 N/mm.

FIGS. 1, 2A and 2B show that the implant 10 can include a skirt 14 (which can also be described as a tab), which may be reinforced with crystalline molded PVA hydrogel material, to provide a means for attaching to vertebral bodies. Typically bone screws (not shown) are placed through the skirt and into underlying local vertebral bodies. However, other fixation means may be used, such as for example, suture anchors, adhesives, and the like. In particular embodiments, the skirt 14 can be between about 1-4 mm thick, typically about 2 mm thick. For the latter, each of the mesh layers can be about 0.75 mm thick. The additional thickness of the skirt 14 can be provided by the molded PVA material that embeds the layers forming the skirt material 14.

Figure 3:
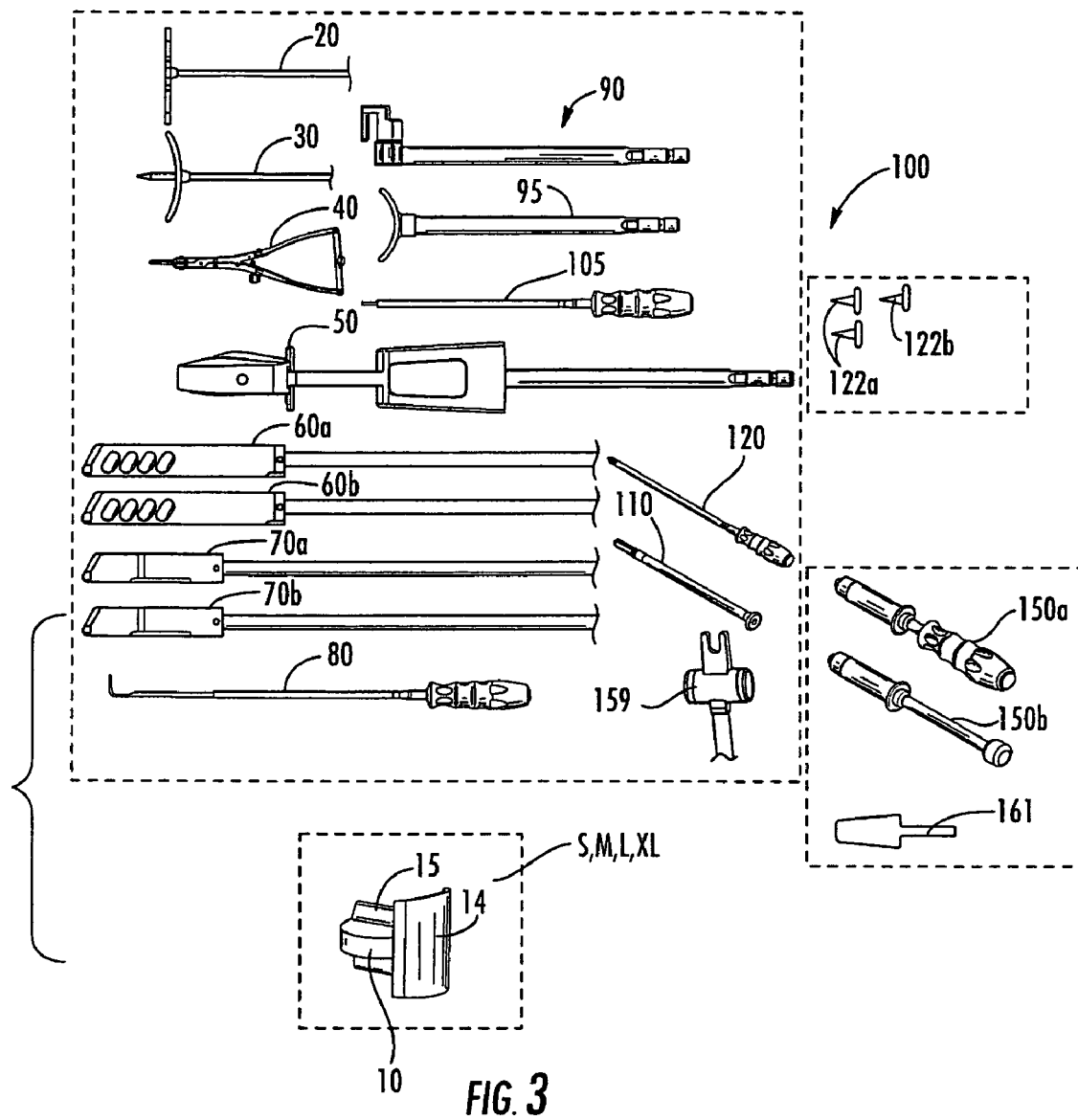
FIG. 3 is a schematic illustration of surgical instruments that can be used to implant a total-replacement spinal disc prosthesis according to embodiments of the present invention.

As shown in FIG. 3, a surgical instrument medical kit 100 can be used to select the correct implant size and/or shape and place the implant 10 in the body. The medical kit 100 can include one or more of the following components, which in particular embodiments, can be arranged in "universal" and size specific trays and/or packaged with an implant 10 as will be discussed further below:

Access Window Tool (AWT) 20;
Discectomy Width Template (DWT) 30;
Distractor 40;
Trials 50;
Chisels 60a, 60b;
Reamers 70a, 70b;
Clearing Hook 80;
Inserter 90;
Pusher 95;
Pilot Hole Punch 105;
Screw Holder 110;
Screwdriver 120;
Screws 122a, 122b;
Mallet 159;

Reamer Cleaning Tool 161;

First Releaseable Handle 150a; and

Second Releasable Handle 150b.

Figures 4A, 4B:
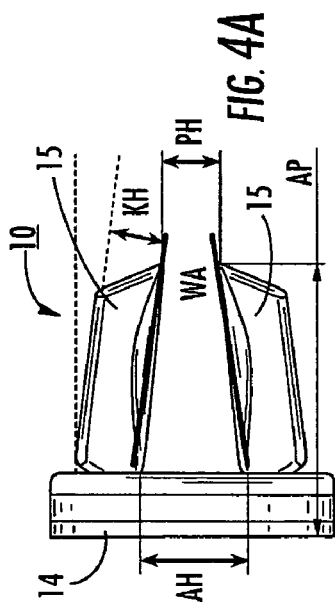
FIG. 4A is a left side view of a spinal implant with nomenclature of certain features identified.
FIG. 4B is a chart of exemplary sizing and dimensions of spinal disc implant configurations/shapes according to embodiments of the present invention.

As shown in FIGS. 4A and 4B, the implant 10 can be made available in a range of different anterior-posterior (AP) sizes with an associated different keel height (the dimensions shown in mm), such as, for example, S, M, L, XL. Each subset of differently sized implants, S, M, L, XL, can have differing dimensions associated with one or more of anterior height (AH), posterior height (PH), keel height (KH) and wedge angle (WA). As shown, in some embodiments, the medium and large implants may have a greater number of size variations and/or combinations of variations than the small and extra large versions. The implants may be alternatively provided in other categories of sizes and/or other dimensions. Other tools may also be included in the kit while some of those shown may be omitted. In some embodiments, the implant 10 may be custom-made for a particular patient. See, e.g., co-assigned, co-pending, U.S. application Ser. No. 11/753,755, the contents of which are hereby incorporated by reference as if recited in full herein. As such, some of the instruments defined above may be optional. Similarly, where alternate fixation techniques are used, bone screw instruments may not be required.

Generally stated, the surgical implantation methodology can be described by the following general steps. Incision and approach to lumbar spine (Step 1). Use the AWT 20 to confirm sufficient approach channel (Step 2). Insert the DWT 30 to mark the space for disc removal (Step 3). Prepare the intervertebral disc space (Step 4). Insert the Spreader/Distractor 40 (Step 5). Choose an appropriate trial 50 size (Step 6) (may include trying several different trials). Insert the trial 50 (Step 7). The trials can perform a supplemental distraction as the space may have a tendency to partially close or collapse after the primary distractor is removed. Cut with the chisels 60a, 60b (Step 8). Cut with the reamers 70a, 70b (Step 9). Clean the chiseled slot with the hook 80 (Step 10). Insert the implant 10 (Step 11). The implant can be forced into position and can also act as a supplemental distractor after the trial is removed to open the disc space to receive the implant without requiring additional tooling to open the space to position the implant 10 (Step 12).

Where desired, punch pilot holes through the skirt 14 and bone (Step 13). Attach bone screws or other fixation members to implant 10 and local bone (Step 14).

FIGS. 5A-5B illustrate an exemplary AWT 20 with a handle 22 on one end portion and a flat or planar plate 21 on the other. The plate 21 corresponds to the access window desired by the orthopedic surgeon. One AWT 20 can be provided or made available for discs of each AP diameter (S, M, L, XL) since the access window for discs of each AP diameter is different.

FIGS. 6A-6C and 7 illustrate an exemplary DWT 30. The DWT 30 includes a shield 31 and an outwardly projecting pin 32 on one end connected to a shaft 33 with a handle 34 on the other end. The pin 32 inserts into the disc prior to discectomy. The pin 32 can have a length "L" of between about 10-30 mm, typically about 20 mm, and a diameter of between about 1-3 mm, typically about 1.8 mm. This allows the surgeon to determine the patient's midline via visualization, such as via X-Ray, by comparing the pin location relative to anatomical features. The shield 31 can have an arcuate shape and serve as a stop to limit over-insertion of the pin 32 posteriorly. The width "W" of the shield 31 is a template that defines the width of disc to be cleared from the disc space during the discectomy. The DWT 30 can be provided in different heights "H", such as about 13 mm for S, about 15 mm for M, and about 17 mm for L and XL. One DWT 30 can be provided or made available for discs of each AP diameter, as the discectomy width for discs of each AP diameter is different. In some embodiments, the overall length of the DWT 30 can be between about 100-300 mm, typically about 200 mm. Next, the intervertebral space can be prepared with conventional instruments as is well known to those of skill in the art.

As shown in FIGS. 8A and 8B, a distractor 40 (also known as a spreader) can be used to spread the vertebral bodies adjacent the target disc space. The distractor 40 can be any conventional distractor. See, e.g., U.S. Pat. No. 7,081,118, the contents of which are hereby incorporated by reference as if recited in full herein. As shown, the distractor 40 can include tip blade portions 41 that remain parallel during spreading, handles $42_1$, $42_2$, a bridge 44 and a hammer engaging member 46 on the bridge 44. The distractor 40 includes a mechanical linkage assembly 47 that engages a spring-loaded lock (nut) 48 that can lock the distractor blades 41 to any open position. The spring 49 can reside between the handles $42_1$, $42_2$. The blades 41 and the handles $42_1$, $42_2$ can be removably attached to opposing end portions of the linkage 47. In this embodiment, the distractor 40 can perform parallel distraction. Referring to FIGS. 9A-9D, the bridge 44 can be removably attached to the handles $42_1$, $42_2$. As shown, the bridge 44 can be slidably attached to one handle $42_1$, pivoted down, then slidably attached to the other handle $42_2$.

Figure 12C:
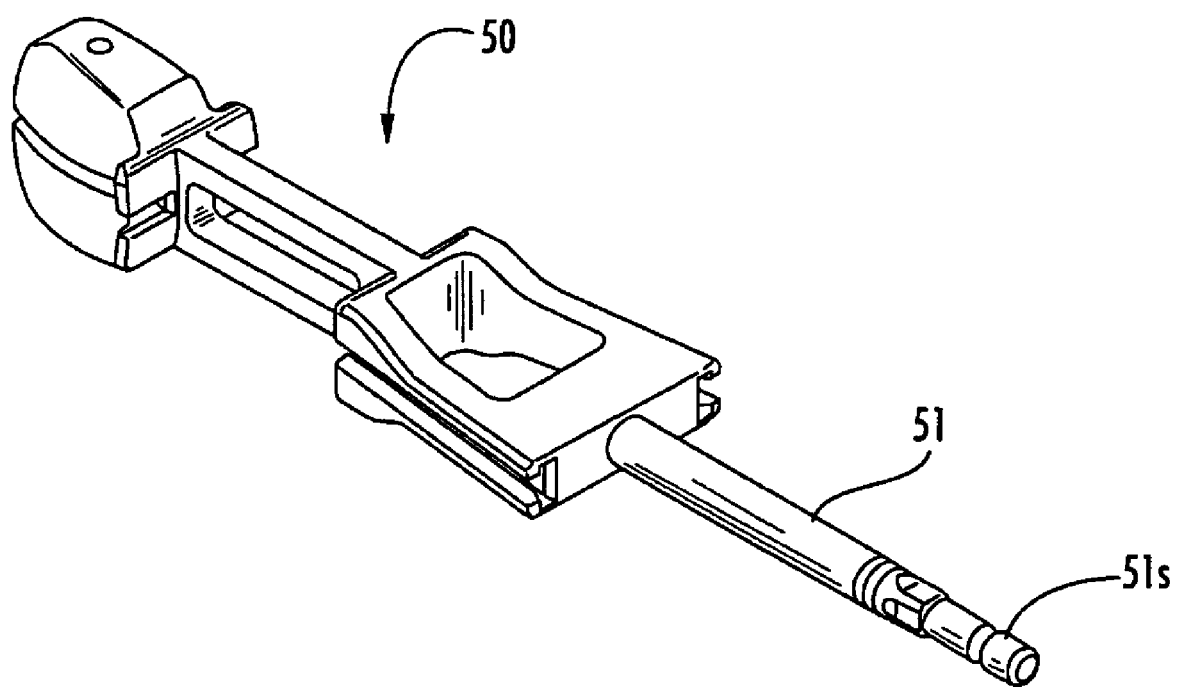
FIG. 12C is a side perspective view of a trial with a shaft stem releasably attachable to different handles according to some embodiments of the present invention.

FIGS. 10A-10C illustrate an exemplary trial 50. The trial 50 includes a shaft 51 that holds a cutter guiding slot 52, an implant member 54 with bearing surfaces 54s, and a fixed AP-stop member 53 with a cutting window 53w. The trial 50 can include a handle 50h that can be configured as a removable trial handle/shaft 150a as shown in FIG. 12C. The handle/shaft 150a can comprise a sterilizable material, such as silicone, for a resusable instrument. The implant member 54 can also include an aperture for positional control under image visualization, such as X-ray. The trial 50 can also be an integrated fixed assembly. Optionally, the implant bearing surfaces 54s can include a shallow clearance groove 55. The optional clearance groove 55 does not function as a cutting "guide" and may be provided in the bearing surface 54s of the trial 50 to allow a lowermost or uppermost portion of the respective chisel 60a, 60b and/or reamer 70a, 70b to pass thereabove or therebelow. The shallow groove 55 (e.g., not contact slot) may be less than about 0.5 mm deep, typically about 0.25 mm deep.

In the embodiment shown, the trial 50 has a shaft 51 with an upper guiding slot or channel 52 for the chisel 60a and reamer 70a and a lower guiding slot or channel 52 for the chisel 60b and the reamer 70b. The guiding slots 52 reside on the shaft 51 of the trial 50, axially spaced apart from the stop 53 and the trial implant portion 54 (they are not on the bearing surface of the trial). The cutting guide slots 52 can be held by respective ramps 58; the upper ramp 58 declines toward the superior surface and the lower ramp 58 inclines toward the inferior surface of the trial implant portion 54. The trial 50 implant portion 54 can have 3D convex contours on the superior and inferior bearing surfaces 54s of the trial, substantially matched to average patient anatomies and disc geometries. The trials 50 can be provided in the same implant widths with sizes varied in other dimensions. In some embodiments, the trials 50 can have a one-to-one correspondence with the corresponding prostheses: one trial implant member portion 54 equals one implantable disc 10 (see, e.g., FIG. 4B) and the shapes substantially correspond to each other (e.g., the size and convexities of the superior and inferior surfaces of the trial corresponds to the selected spinal implant). In other embodiments, trials 50 may be adjustable, or can be "built", or are variable by one parameter only (such as height). The trial 50 (and implant 10) can each function as a supplemental distractor during use to open the target disc space which may partially collapse and/or partially close after removal of the primary distractor 40. That is, the mallet can force the trial 50 (and implant) into position and thereby force the adjacent vertebral bodies further apart to snugly receive the trial 50 (and subsequently the implant 10) without requiring the use of any additional instruments to maintain the disc space during trialing or implanting (e.g., the trial and implant are self-distracting).

FIGS. 11B and 11C illustrate that the stop 53 can include anchoring portions 57 such as pins or teeth or other features that extend toward the trial implant portion 54 that can engage and/or anchor to local vertebrae. In the embodiment shown, the anchoring portions 57 comprise two outwardly extending teeth, one on each side of the window 53w to facilitate the trial biting into and/or engaging the anterior side of the vertebral bodies for the purpose of limiting motion of the trial and/or maintaining trial position during the chiseling and reamer steps.

FIG. 11A shows that the lead in portions 52i of the slots 52 can be configured with a geometry that snugly matably engages that of a corresponding portion of the cutters (chisel and reamer) for positive orientation and alignment during cutting. Similarly, FIG. 11C illustrates that the window 53w can provide the geometric lead-in shapes for the cutting blades (60a, 70a) in a lateral and a caudal-cranial direction and that the geometry can be configured to snugly and/or matably receive the lower or upper leading ends of the blades (depending on if an upper or lower keelway is being cut) (61s, 71s, FIGS. 15A, 16A).

FIGS. 12A and 12B illustrate the trial 50 being inserted into position according to some embodiments of the present invention. A mallet 159 can be used to advance the implant portion 54 into position with the upper and lower stops 53 resting against the outer surfaces of the respective vertebral bones.

Figure 12D:
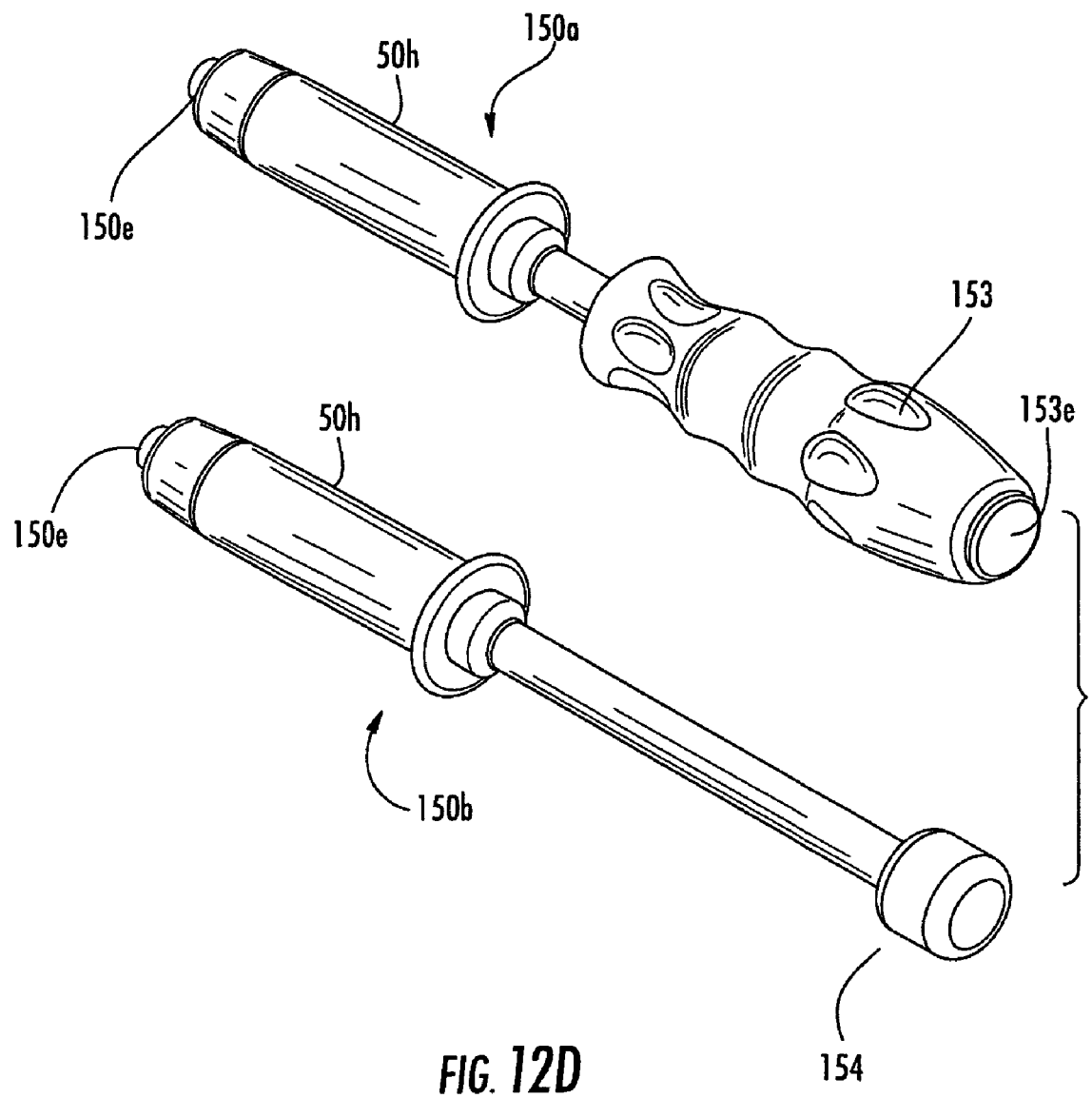
FIG. 12D is a side perspective view of two different handles that can releasably attach to the trial shown in FIG. 12C (and/or other instruments) according to embodiments of the present invention.

FIG. 12C illustrates a trial 50 with a shaft 51 having a shaft stem 51s that releasably engages different handles 50h. For example, as shown in FIG. 12D, the trial stem 51s can serially attach to first and second releasably attachable handles 150a, 150b. The trial 50 can also attach to the second handle 150b, to allow for the mallet 159 to cooperate with the second handle for ease of extraction of the trial 50. The first handle 150a can have an end portion that cooperates with the mallet 159 while the second handle 150b can have an end portion that allows for cooperation with a mallet in the reverse direction from that of the first handle 150a. The attachment means between stem 51s and engaging end 150e of the handle 50h can be any suitable means, including bayonet, frictional press-fit, threads, or the like. As shown, the first handle 150a has a rubber grip handle 153 with a rigid end 153e for engaging the mallet 159. The other handle 150b can have a knob 154 for "hammering" out or extracting the trial 50 from the disc space (e.g., for removing the trial rather than inserting the trial as per handle 150a). In some embodiments, one or both of the handles 150a, 150b can releasably attach to other instruments and the other instruments can have a stem 51s similar to that shown with respect to the trial 50 in FIG. 12C. For example, the pusher 95 and inserter 90 can all attach to the first handle 150a.

FIGS. 13A-13D illustrate the use of a cutter or chisel blades 60a, 60b to cut the keelways or mortises in the vertebral bones. In operation, the cutting blade (e.g., chisel and/or reamer) extends into inetevertebral bone and a lower portion thereof may travel over the bearing surface 54s in the intevertebral space, but typically does not contact the bearing surface 54s of the trial 50.

A set of trials can be provided, where each trial 50 can incorporate a unique geometry relative to the geometry of the other trials in the set which, when used with a common "universal" chisel and/or "universal" reamer or other "universal" cutting device, can yield a unique keelway height and depth cut into the vertebral bodies. In other words, in some embodiments, each trial 50 can incorporate a fixed stop location 59 that cooperates with a fixed stop segment of the cutter, such as chisel stop portion 63 and reamer stop portion 73 (FIGS. 13B, 16A) on the respective chisel and reamer. The position of the fixed stop location 59 can be defined by the ramp 58. As shown in FIGS. 13B and 16A, the fixed ramp stop location 59 can be proximate a lead-in portion of the ramp 58 and defined by the geometry of the slot 52 and geometry of the stop portion 63, 73 of the respective cutter. However, the fixed stop location 59 may be positioned in other locations, such as, for example, on the window 53 or at a different location along the ramp 58. It is noted that although chisels and reamers are described as suitable bone cutting devices, saws (blades) or other devices may also or alternatively be used.

In some embodiments, each trial 50 can be configured to be different to allow for different cut heights and depths into the target vertebral body. Also, the plane of the ramp 58 can be considered to be "sunken" relative to the bearing surface 54s of the trial. Each trial 50 can incorporate a different sunken depth of this plane, which allows for a unique keelway height to be cut into the vertebral body.

Figure 14:
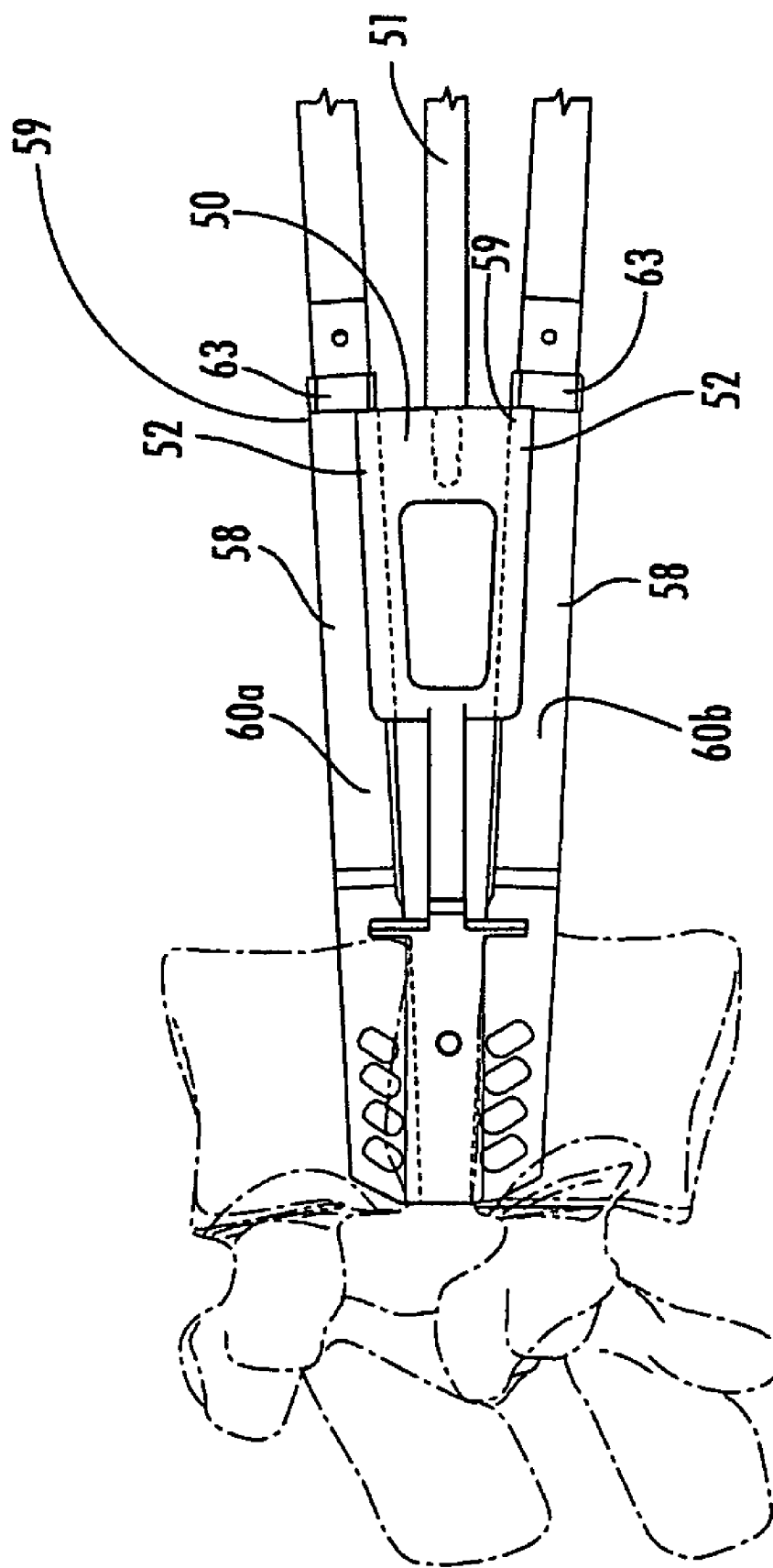
FIG. 14 is a partially translucent side view of two chisels in the fully extended position in upper and lower keelways with the trial in the intervertebral disc (IVD) space according to some embodiments of the present invention.

Referring again to FIGS. 13A-13D, chisels 60a, 60b are used to cut the desired keelways. The cutting can be carried out serially as shown in FIGS. 13A-13D, with the top cutter 60a typically used first and kept in position until the bottom cutter 60b is extended to stabilize the trial 50 as shown in FIG. 14. However, the bottom cutter (e.g., chisel) 60b may be used first, with the upper cutter 60a following behind. It is noted that the schematic illustration of the vertebrae and the extended cutters 60a, 60b in FIG. 14 is not to scale (and XL trial is shown); however, a smaller trial may be more appropriate in the vertebrae shown.

FIGS. 15A and 15B show an example of a chisel 60a, 60b. The leading edge 62 can be beveled or have a chamfer 62b. A series of apertures 64 can be used to trap or remove chiseled bone. The blade 60a, 60b can also include a segment with a formed ledge 66 located axially rearward of the cutting portion of the chisel 61 that matably engages slot 52 in the ramp 58 of the trial 50. As shown in FIGS. 13C and 13D, the formed ledge 66 typically does not extend through window 53w during cutting as only the cutting end portion 61 extends into the vertebral bone to cut the keelway.

Figure 16D:
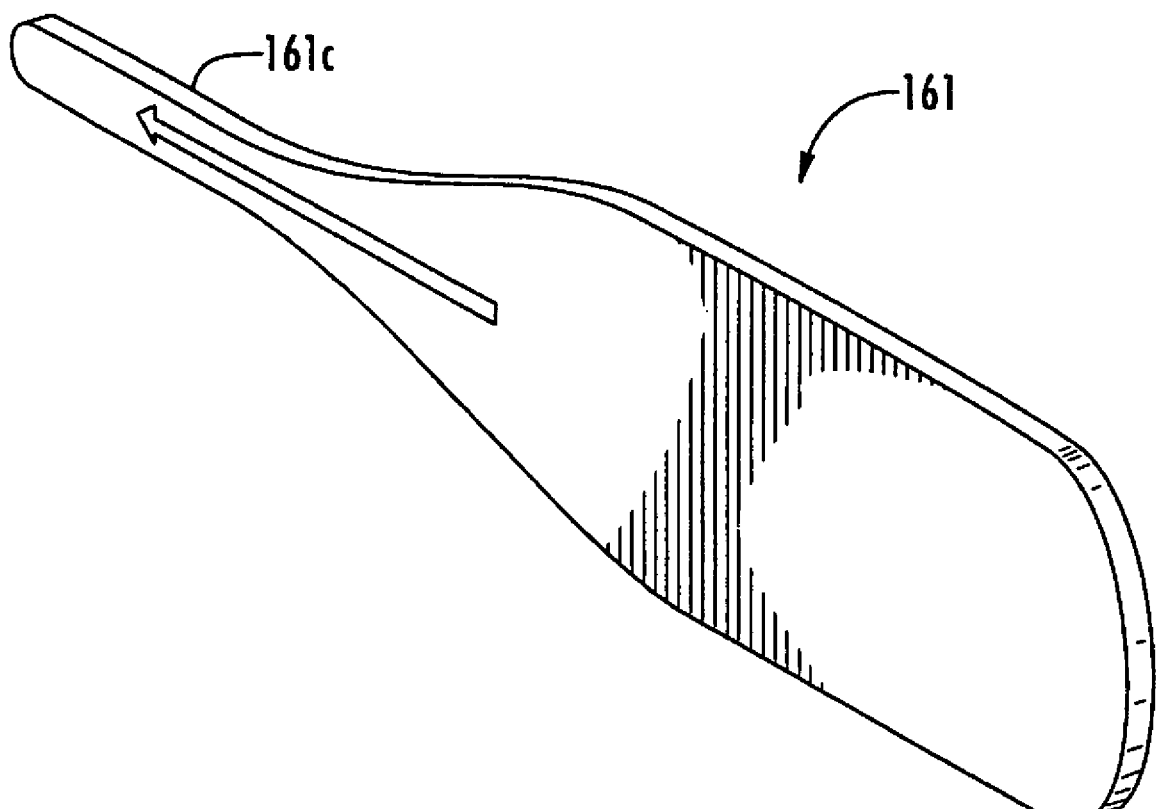
FIG. 16D is a side perspective view of a reamer-cleaning tool that can be used to clean a forward cutting portion of a respective reamer according to embodiments of the present invention.

FIGS. 16A-16C illustrate a similar configuration for the reamer 70a, 70b. As the reamers 70a, 70b are primarily used to "square" up the keelways, apertures are not required. Indeed, the reamers 70a, 70b may not be required in some embodiments as the chisels 60a, 60b (or other cutting devices) may form sufficiently open keelways (particularly for flexible keels). However, the cutting end portion 72 of the reamers 70a, 70b may be configured with a beveled edge 72b and may include a small gap 72g or mismatch between two cutting blades 74, 75 to allow bone to enter therein. As shown in FIG. 16D, a thin reamer-cleaning tool 161 with a cleaning segment 161c can be inserted into the gap 72g to clean the reamer. The blade 70a, 70b can also include a segment with a formed ledge 76 located axially rearward of the cutting portion of the reamer 71 that matably engages slot 52 in the ramp 58 of the trial 50. As shown in FIG. 16A, the formed ledge 76 typically does not extend through window 53w during cutting as only the cutting end portion 72 extends into the vertebral bone to cut the keelway.

FIG. 16A illustrates that the top reamer 70a slides through the guides 52 to ream the keelway 10k, and remains in position while the bottom reamer 70b slides through its respective guide 72 to ream the lower keelway. The cutting ends (blades) of the reamer 70a, 70b and chisel 60a, 60b can be configured to be replaceable with the devices being multi-use/reusable after sterilization.

Note that the order of cutting is typically to (a) use one chisel cutter 60a and leave the chisel cutter 60a in position, (b) insert the second chisel cutter 60b, (c) remove the second cutter 60b, (d) insert the first reamer 70a while the first cutter 60a is still in position, (e) remove the first chisel cutter 60a, and (f) insert the second reamer 70b while the first reamer 70a is still in position.

Figure 17:
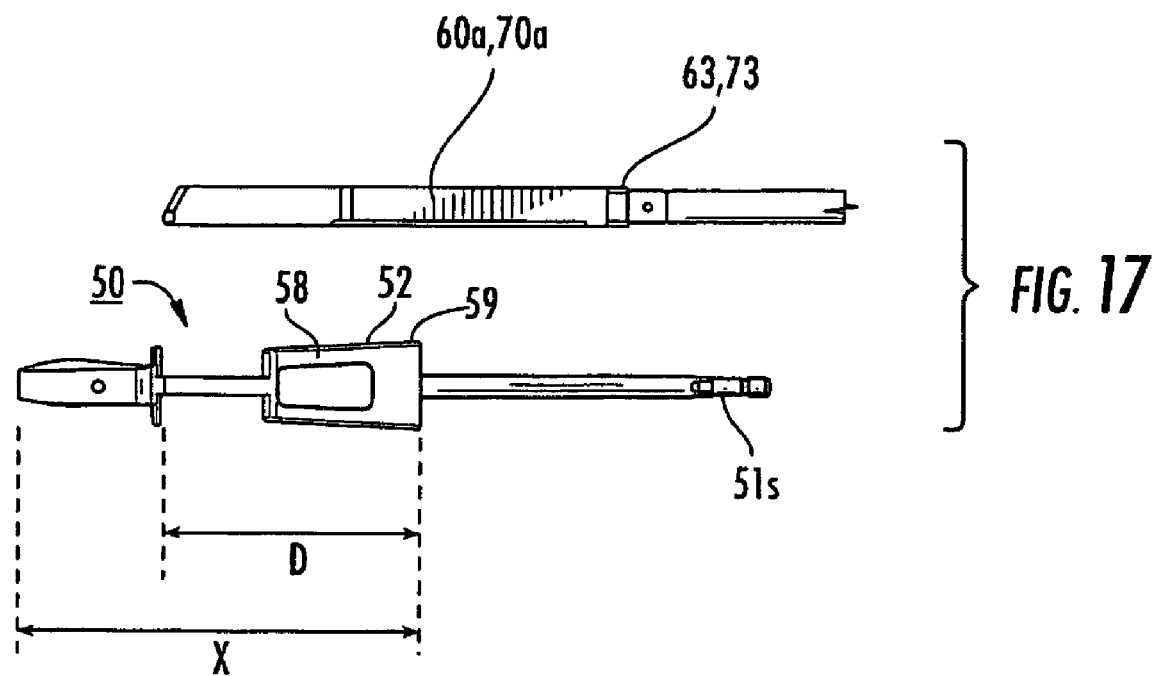
FIG. 17 is a side schematic illustration of a trial with a universal cutter having a fixed stroke distance "X" whereby different trials provide different lengths "D" according to some embodiments of the invention.

Referring to FIG. 17, it is noted that in some embodiments, a universal chisel 60a, 60b and/or reamer 70a, 70b can be used with any of the trials 50. In so doing, each trial can have a different distance "D" that corresponds the distance between the anterior portion or side of the trial implant 54 and stop 53 and the cutting blade stop location 59 on the respective ramp 58; however, the overall length "X" can be substantially constant for all of the trials 50, allowing the use of a common or "universal" chisel and/or reamer. That is, the trials 50 can have different lengths from a proximal side of the ramp 59 to an anterior stop 59 of the trial thereby allowing the use of a common reamer and/or chisel for each of the various trials.

Figure 19:
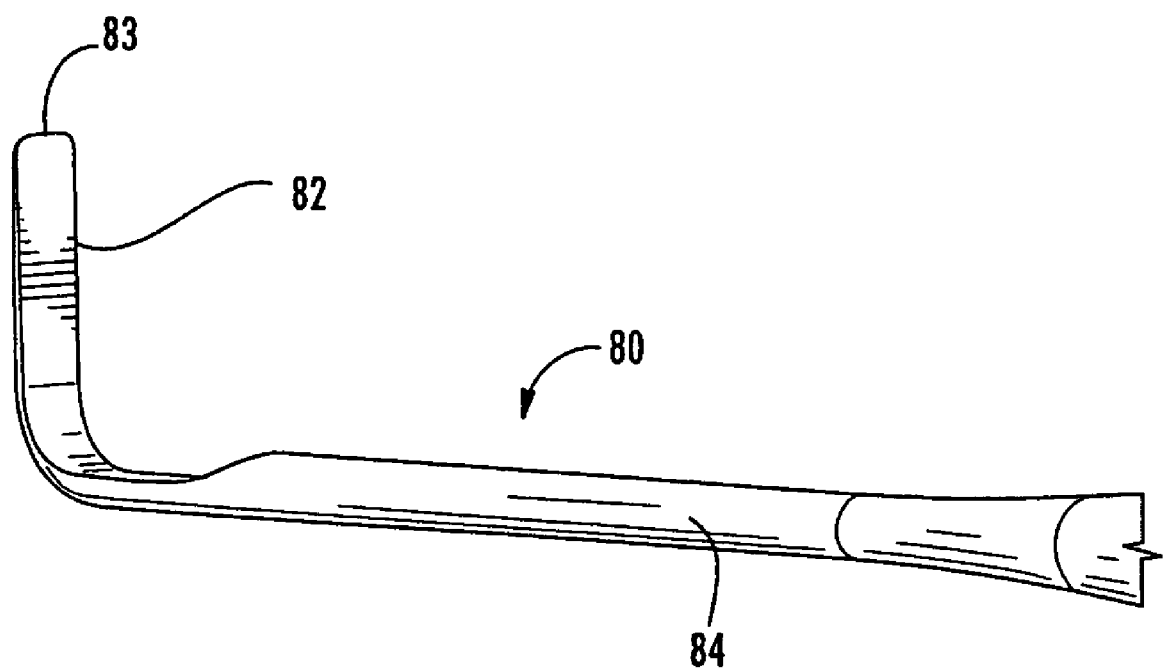
FIG. 19 is a greatly enlarged partial view of the cleaner shown in FIGS. 18A and 18B.
Figure 21A:
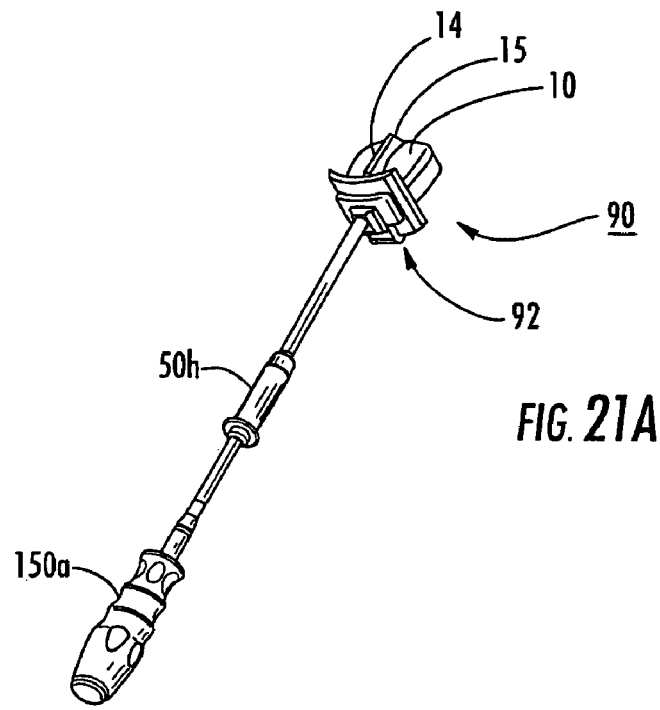
FIG. 21A is a side perspective view of an inserter with implant illustrating the inserter holding the implant according to embodiments of the present invention.
Figures 21B, 21C:
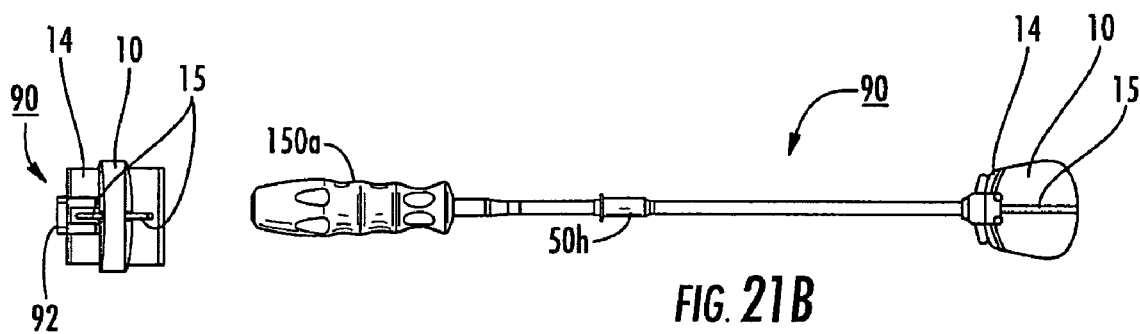
FIG. 21B is a bottom view of the device with implant shown in FIG. 21A.
FIG. 21C is an end view of the device shown in FIG. 21B.
Figure 21D:
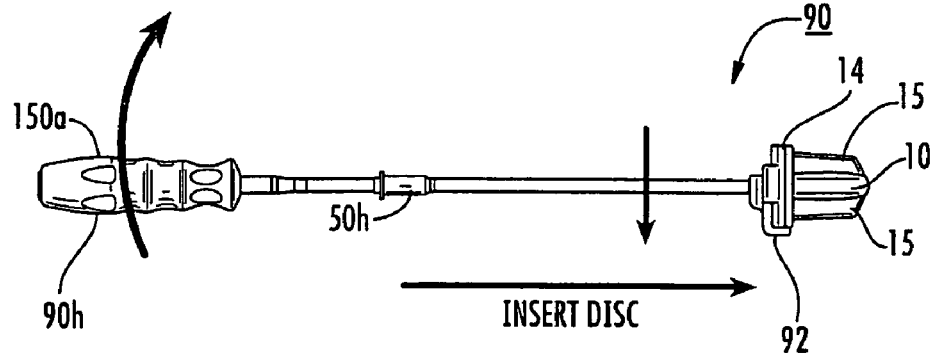
FIG. 21D is a side view of the device with implant shown in FIG. 21A.

As shown in FIGS. 18A and 18B, a clearing hook 80 can be used to clear debris that remains in the keelways. The clearing hook 80 is not designed as a scraper/cutter. As shown in FIG. 19, the clearing hook 80 can have a shaft 84 that merges into a handle 85 at one end and that merges into a substantially planar segment 82 that is substantially orthogonal to the primary shaft 84 and has rounded outer edges 83. The width of the rounded edge can be between about 2-3 mm.

Referring to FIGS. 20A-20D, an exemplary inserter 90 is shown. The inserter 90 has an implant holder head 90h. The head 90h has a skirt channel 91 that releasably engages the skirt 14 of implant 10 (FIGS. 1, 2A). The inserter 90 is configured to allow a user to slide the instrument 90 sideways to release the implanted product 10 (once implanted in the IVD space), or to torque it over (as with a claw hammer working on a nail) to pry the instrument 90 away from the implanted device 10. One inserter 10 can be configured to hold and implant al of the disc sizes of a substantially common AP diameter. The inserter head 90h can be formed from an elastomeric and/or metallic material.

As shown in FIGS. 21A-21D, the inserter 90 is typically oriented so that a closed floor 92 of the skirt channel 91 is under the lower portion of the bottom skirt 14. After "straight" insertion, typically in the orientation shown in FIG. 21D, the handle 90h of the inserter 90 can be rotated to rotate the inserter about the implant 10 (shown by the arrow proximate the handle in FIG. 21D) to release the inserter 90 from the implant 10, leaving the implant 10 in position. Stated different, in some embodiments, the release of the implant 10 from the inserter 10 can use rotation due to the flexibility of the skirt 14. However, in other embodiments, the implant 10 can be released by sliding the inserter 90 downward (which in this case does require that the skirt flex)—as indicated by the down arrow proximate the channel 91 in FIG. 21D. The latter operation may employ some clearance for the inserter, which may not be possible in some applications due to the typically small size of the surgical windows.

Figure 22:
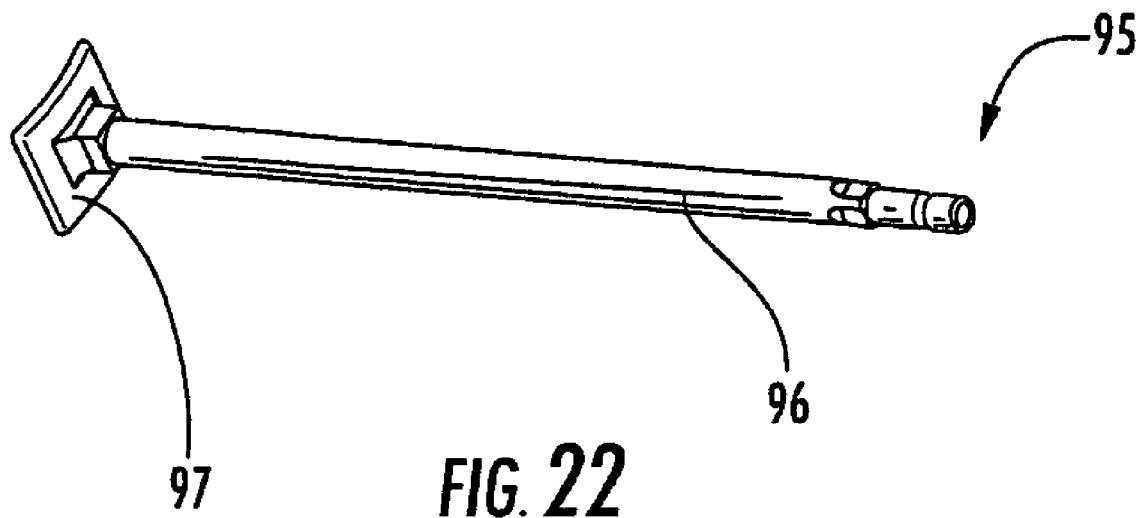
FIG. 22 is a side perspective view of a pusher according to embodiments of the present invention.

FIG. 22 illustrates that a pusher 95 can be used to further push the implant 10 into a desired position in the target IVD space. The pusher 95 includes a shaft 96 and a shield 97 that pushes against the implant 10.

Figure 23:
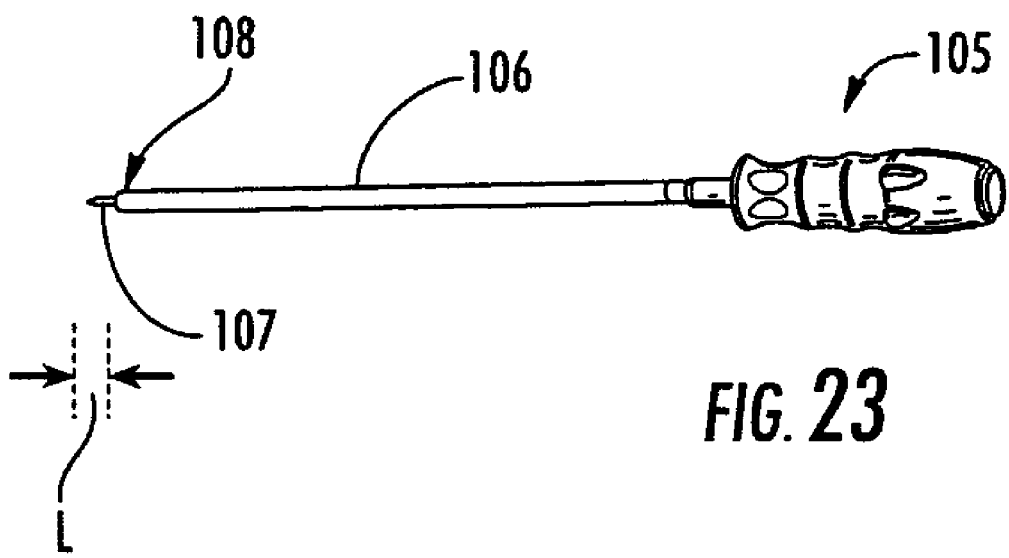
FIG. 23 is a side perspective view of a pilot-hole punch according to embodiments of the present invention.

FIG. 23 illustrates a pilot hole punch 105. The punch 105 includes a shaft and a sharp punch end 107. The punch length "L" of the punch end 107 is greater than the thickness of the implant skirt 14 and the thickness of the cortical layer of bone to ensure that the cortical layer is punched through. The punch length "L" can be between about 5-15 mm, which is typically longer than the penetrating length, which is typically between about 3-10 mm (so as to be able to penetrate the skirt 14). The punch end 107 merges into a fixed stop 108 to ensure that the punch 107 is not over-inserted into the bone posteriorly. The punch 105 can be used to insert apertures into the skirt and/or underlying bone. Typically, four holes are punched into the bone and skirt for receiving anchoring members such as bone screws, but the skirt 14 may be preformed with the holes.

Figure 26B:
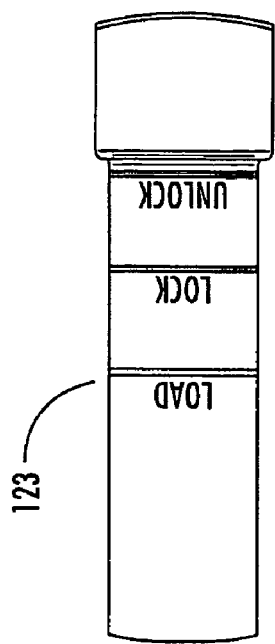
FIG. 26B is a partial enlarged view of the operational functional bands shown in FIG. 26A.
Figure 26A:
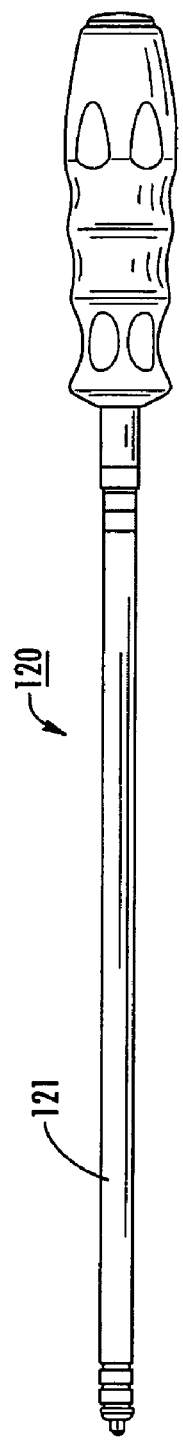
FIG. 26A is a side view of the device shown in FIG. 25.
Figure 25:
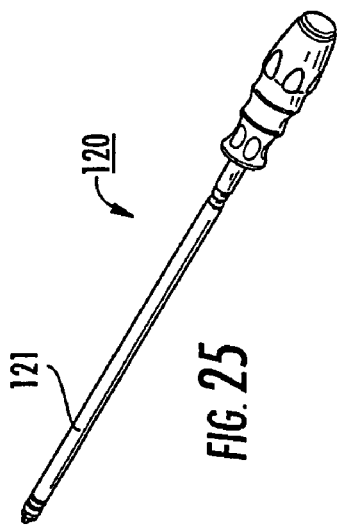
FIG. 25 is a side perspective view of a hex screwdriver according to embodiments of the present invention.

FIGS. 24A-24E illustrate a screw holder 110 that holds a screw at a distal screw cavity portion 112. The screw holder 110 cooperates with a hex screwdriver 120 (FIG. 25, FIGS. 26A, 26B). That is, the shaft 121 of the hex screwdriver is configured to reside in a channel 111 in the screw holder 110 to allow the screwdriver 120 to advance and rotate to tighten a target screw held in cavity 112 against the skirt 14 (FIG. 1) and into underlying bone, while the screw is positively retained by the holder 110. The holder 110 can be disengaged when the screw is partially engaged with bone. As shown in FIGS. 26A and 26B, the screwdriver 120 can incorporate color-coded bands 123. At least one of the bands 123 shows through a window or is otherwise visible when in the screw holder 110 for each position of the holder 110 relative to the screwdriver: e.g., Load, Lock, Unlock, although other words, indicia, such as arrows or combinations thereof can be used to indicate the desired operation (e.g., Assemble, Lock, Release). With the hex head of the screwdriver 120 inserted into the hex receptacle of the screw, the holder 110 holds the screw on the outer diameter of the head. A user can turn the screwdriver 120 in the holder 110 to select the desired operation to carry out the associated operation: for example, to load a screw into the device 110, lock the screw in the device 110, then unlock the holder 110 after the screw is assembled to the implant 10.

The distractor 40 (and its components, e.g., blades, handles, bridge) may be provided as a single universal device in the medical kit. The pusher 95, mallet 159, pilot hole punch 105, screwdriver 120 and holder 110 may be provided as universal components (e.g., a single one of each). Screws, where used, can be provided in at least two sizes 122a, 122b (FIG. 3) to allow for an increased size that can be used where the smaller one is stripped. The screws 122a, 122b can be packaged and/or provided with the implant 10 or with the instrument kit 100. Similarly, a single removable trial handle/shaft 150a can be provided to mate with all of the trials 50. The inserter 90 can be provided in S, M, L, and XL. A universal medical tray (not shown) can be provided that packages the universal instruments together. Additionally, for convenience, pre-assembled trays of small instruments, medium instruments, large instruments, and extra large instruments can be selected and provided, each for a target site(s) such as L4/L5. The trials 50 and implants 10 can be in 23 different sizes and configurations, and they can be sub-grouped into the S, M, L and XL categories for easier selection and/or use by a clinician.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A trial for spinal surgery, comprising:
    a trial implant portion having a shape corresponding to an implantable spinal disc implant;
    a shaft connected to the trial implant portion; and
    at least one axially extending cutting guide attached to the shaft at a position that is axially spaced apart from the trial implant portion, the cutting guide configured to releasably slidably receive and guide a cutting member toward vertebral bone,
    wherein the at least one cutting guide comprises a superior cutting guide and an inferior cutting guide, each with a respective cutting guide slot, wherein the trial further comprises an upper and lower trial implant portion stop with a respective alignment window residing respectively above and below the bearing surfaces on an anterior side of the trial implant portion, whereby the upper and lower alignment windows are configured to allow cutting members to extend therethrough while held in a desired orientation by the corresponding superior and inferior cutting guide slot.

2. A trial according to claim 1, wherein the trial implant has superior and inferior bearing surfaces that are devoid of cutting guide slots.

3. A trial according to claim 1, wherein the at least one axially extending cutting guide comprises an upper cutting guide slot and a lower cutting guide slot, the upper and lower guide slots residing on diametrically opposed sides of the shaft.

4. A trial according to claim 1, wherein the at least one cutting guide comprises a slot with a geometry configured to maintain positive orientation of a cutting blade as the cutting member slidably advances therein, and wherein the at least one cutting guide slot is configured to define a non-adjustable fixed cutter stop that engages a stop portion of a cutting member that slidably advances therethrough to prevent further forward movement of the cutting member.

5. A trial according to claim 1, further comprising first and second outwardly projecting anchoring portions residing on a side of the trial implant portion stop facing the trial implant portion, the anchoring portion configured to engage an anterior side of a target vertebral body, thereby limiting motion of the trial and/or maintaining trial position during formation of keelways into the vertebral body.

6. A trial according to claim 1, further comprising a shallow groove on the superior and inferior bearing surfaces of the trial implant portion, the shallow groove configured so as to avoid contact with the cutting blade during formation of a keelway.

7. A trial according to claim 1, in combination with a chisel, the chisel being the cutting member that slides in the cutting guide, the chisel having a stop portion residing axially away from a forward edge portion of the chisel, wherein the chisel stop portion cooperates with a leading edge portion of a slot in the cutting guide to prevent forward motion of the chisel when the chisel stop portion engages the leading edge portion of the slot of the cutting guide.

8. A trial according to claim 7, in further combination with a reamer, the reamer being the cutting member that slides in the cutting guide, the reamer having a stop portion residing axially away from a forward edge portion of the reamer, wherein the reamer stop portion cooperates with a leading edge portion of a slot in the cutting guide to prevent forward motion of the reamer when the reamer stop portion engages the leading edge portion of the slot of the cutting guide.

9. A trial according to claim 1, in combination with a pair of universal reamers and a pair of universal chisels, wherein the at least one cutting guide is two cutting guides, one for directing one of the reamers and chisels to form a superior keelway and the other for directing the other one of the reamers and chisels to form an inferior keelway, wherein the reamers and the chisels are cutting members that releasably and slidably engage the cutting guides.

10. A trial according to claim 1, wherein the shaft merges into a handle, and wherein the handle and shaft are releasably attached to the trial implant portion.

* * * * *